US007342099B2

(12) United States Patent
Thorgeirsson et al.

(10) Patent No.: US 7,342,099 B2
(45) Date of Patent: Mar. 11, 2008

(54) CDNA ENCODING A GENE BOG (B5T OVER-EXPRESSED GENE) AND ITS PROTEIN PRODUCT

(75) Inventors: Snorri S. Thorgeirsson, Bethesda, MD (US); Joseph T. Woitach, North Bethesda, MD (US); Minghuang Zhang, Gaithersburg, MD (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 524 days.

(21) Appl. No.: 10/772,988

(22) Filed: Feb. 5, 2004

(65) Prior Publication Data

US 2004/0139485 A1    Jul. 15, 2004

Related U.S. Application Data

(60) Division of application No. 09/637,746, filed on Aug. 11, 2000, now Pat. No. 6,727,079, which is a continuation of application No. PCT/US99/04142, filed on Feb. 25, 1999.

(60) Provisional application No. 60/079,567, filed on Mar. 27, 1998, provisional application No. 60/075,922, filed on Feb. 25, 1998.

(51) Int. Cl.
C07K 14/00     (2006.01)
(52) U.S. Cl. .................. 530/350; 530/402; 530/828; 435/7.1
(58) Field of Classification Search ............... 530/350, 530/402, 828; 435/7.1
See application file for complete search history.

(56) References Cited

U.S. PATENT DOCUMENTS

| | | | |
|---|---|---|---|
| 4,224,179 A | 9/1980 | Schneider | |
| 4,231,877 A | 11/1980 | Yamauchi et al. | |
| 4,235,871 A | 11/1980 | Papahadjopoulos et al. | |
| 4,247,411 A | 1/1981 | Vanlerberghe et al. | |
| 4,394,448 A | 7/1983 | Szoka, Jr. et al. | |
| 4,399,216 A | 8/1983 | Axel et al. | |
| 4,673,567 A | 6/1987 | Jizomoto | |
| 4,676,980 A | 6/1987 | Segal et al. | |
| 4,736,866 A | 4/1988 | Leder et al. | |
| 4,753,788 A | 6/1988 | Gamble | |
| 4,814,270 A | 3/1989 | Piran | |
| 4,816,567 A | 3/1989 | Cabilly et al. | |
| 4,870,009 A | 9/1989 | Evans et al. | |
| 4,897,355 A | 1/1990 | Eppstein et al. | |
| 5,010,182 A | 4/1991 | Brake et al. | |
| 5,188,943 A * | 2/1993 | Florkiewicz et al. ....... | 435/69.4 |
| 5,364,934 A | 11/1994 | Drayna et al. | |
| 5,376,542 A | 12/1994 | Schlegal | |
| 5,625,031 A | 4/1997 | Webster et al. | |
| 5,631,144 A | 5/1997 | Lemoine et al. | |

FOREIGN PATENT DOCUMENTS

| | | |
|---|---|---|
| EP | 0 036 776 A2 | 9/1981 |
| EP | 0 073 657 A1 | 3/1983 |
| EP | 0 117 058 A2 | 8/1984 |
| EP | 0 177 060 A2 | 8/1984 |
| EP | 0 362 179 A2 | 4/1990 |
| GB | 2 211 504 A | 7/1989 |
| WO | WO 87/05330 | 9/1987 |
| WO | WO 89/05859 | 6/1989 |
| WO | WO 90/13646 | 11/1990 |
| WO | WO 91/00360 | 1/1991 |
| WO | WO 92/20373 | 11/1992 |
| WO | WO 93/08829 | 5/1993 |

OTHER PUBLICATIONS

Phillips et al, 1997, J Gen Virol, 78 (pt 4): 905-9.*
Seville et al, 2005, Current Cancer Drug Targets, 5: 159-170.*
Ahn, A. et al., "The structural and functional diversity of dystrophin", *Nature Genetics*, 3:283-291 (Apr. 1993).
Aplin, J. et al., "Preparation, Properties, and Applications of Carbohydrate Conjugates of Proteins and Lipids", *CRC Critical Reviews™ in Biochemistry*, pp. 259-306 (May 1981).
Attisano, L. et al., "Signal Transduction by Members of the Transforming Growth Factor-β Superfamily", *Cytokine & Growth Factor Reviews*, vol. 7, No. 4, pp. 327-339 (Dec. 1996).
Barrack, E., "TGFβ in Prostate Cancer: A Growth Inhibitor that Can Enhance Tumorigenicity", *The Prostate*, vol. 31, No. 1, pp. 61-70 (Apr. 1, 1997).
Bernards, R. et al., "Structure and expression of the murine retinoblastoma gene and characterization of its encoded protein", *Proc. Natl. Acad. Sci. USA*, vol. 86, pp. 6474-6478 (Sep. 1989).
Boerner, P. et al., "Production of Antigen-Specific Human Monoclonal Antibodies from in Vitro-Primed Human Splenocytes", *The Journal of Immunology*, vol. 147, No. 1, pp. 86-95 (Jul. 1, 1991).
Bowie et al., "Deciphering the Message in Protein Sequences: Tolerance to Amino Acid Substitutions", *Science*, 247:1306-1310 (Mar. 16, 1990).
Bradley, J.E. et al., "A Simple, Rapid Method for the Purification of Poly A⁺ RNA", *BioTechniques*, vol. 6, No. 2, pp. 114-116 (Feb. 1988).
Bradley A., "Production and analysis of chimaeric mice", *Teratocarcinomas and Embryonic Stem Cells: A Practical Approach*, Chapter 5, pp. 113-151 E.J. Robertson, ed. IRL, Oxforrd, (1987) IRL, Oxforrd, (1987).

(Continued)

Primary Examiner—Larry R. Helms
Assistant Examiner—Minh-Tam Davis
(74) Attorney, Agent, or Firm—Merchant & Gould P.C.

(57) ABSTRACT

Nucleic acids that encode novel polypeptides, designated in the present application as "BOG" (B5T Over-expressed Gene) are provided. BOG binds to pRb and is over-expressed in a number transformed rat liver epithelial (RLE) cell lines resistant to the growth inhibitory effect of TGF-β1 as well as in primary liver tumors. Compositions including BOG chimeras, nucleic acids encoding BOG and antibodies to BOG are also provided. Methods of using BOG to modulate pRb-protein interactions and to alter cellular phenotype are further provided.

20 Claims, 20 Drawing Sheets

OTHER PUBLICATIONS

Brodeur, B. et al., "Mouse-Human Myeloma Partners for the Production of Heterohybridomas", *Monoclonal Antibody Production Techniques and Application, Immunology Series*, vol. 33, pp. 51-63, Marcel Dekker, Inc., New York (1987).

Burgess, W. et al., "Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue", *The Journal of Cell Biology*, 111:2129-2138 (Nov. 1990).

Carter, P. et al., "Improved oligonucleotide site-directed mutagenesis using M13 vectors", *Nucleic Acids Research*, vol. 13, No. 12, pp. 4431-4443 (1985).

Cawthon, R. et al., "cDNA Sequence and Genomic Structure of *EV12B*, a Gene Lying within an Intron of the Neurofibromatosis Type 1 Gene", *Genomics*, 9:446-460 (1991).

Chang A. et al., "Phenotypic expression in *E. coli* of a DNA sequence coding for mouse dihydrofolate reductase", *Nature*, vol. 275, pp. 617-624 (Oct. 19, 1978).

Clarke, A. et al., "Requirement for a functional *Rb-1* gene in murine development", *Nature*, vol. 359, pp. 328-330 (Sep. 24, 1992).

Cole, S.P.C. et al., "The EBV-Hybridoma Technique and its Application to Human Lung Cancer", *Monoclonal Antibodies and Cancer Therapy*, pp. 77-96 (1985 Alan R. Liss, Inc.).

Couture, L. et al., "Anti-gene therapy: the use of ribozymes to inhibit gene function", *Trends in Genetics*, vol. 12, No. 12, pp. 510-515 (Dec. 1996).

David, G. et al., "Protein Iodination with Solid State Lactoperoxidase", *Biochemistry*, vol. 13, No. 5, pp. 1014-1021 (Feb. 26, 1974).

de Boer, H. et al., "The *tac* promoter: A functional hybrid derived from the *trp* and *lac* promoters", *Proc. Natl. Acad. Sci. USA*, vol. 80, No. 1, pp. 21-25 (Jan. 1983).

Evan G. et al., "Isolation of Monoclonal Antibodies Specific for Human *c-myc* Proto-Oncogene Product", *Molecular and Cellular Biology*, vol. 5, No. 12, pp. 3610-3616 (Dec. 1985).

Ewen, M. et al., "Molecular Cloning, Chromosomal Mapping, and Expression of the cDNA for p107, a Retinoblastoma Gene Product-Related Protein" *Cell*, vol. 66, pp. 1155-1164 (Sep. 20, 1991).

Felgner, P. et al., "Lipofection: A highly efficient, lipid-mediated DNA-transfection procedure", *Proc. Natl. Acad. Sci USA*, vol. 84, pp. 7413-7417 (Nov. 1987).

Field, J. et al., "Purification of a *RAS*-Responsive Adenylyl Cyclase Complex from *Saccharomyces cerevisiae* by Use of an Epitope Addition Method", *Molecular and Cellular Biology*, vol. 8, No. 5, pp. 2159-2165 (May 1988).

Field, S. et al., "E2F-1 Functions in Mice to Promote Apoptosis and Suppress Proliferation", *Cell*, vol. 85, No. 4, pp. 549-561 (May 17, 1996).

Garfield, S. et al., "Neoplastic Transformation and Lineage Switching of Rat Liver Epithelial Cells by Retrovirus-Associated Oncogenes", *Molecular Carcinogenesis*, vol. 1, No. 3, pp. 189-195 (1988).

Gething, M. et al., "Cell-surface expression of influenza haemagglutinin from a cloned DNA copy of the RNA gene", *Nature*, vol. 293, No. 5834, pp. 620-625 (Oct. 22, 1981).

Gillies, S. et al., "Antigen Binding and biological activities of engineered mutant chimeric antibodies with human tumor specificities", *Hum. Antibod. Hybridomas*, 1(1):47-52 (1990).

Goeddel, D. et al., "Direct expression in *Escherichia coli* of a DNA sequence coding for human growth hormone", *Nature*, vol. 281, No. 5732, pp. 544-548 (Oct. 18, 1979).

Goeddel, D. et al., "Synthesis of human fibroblast interferon by *E. coli*", *Nucleic Acids Research*, vol. 8, No. 18, pp. 4057-4074 (Sep. 25, 1980).

Goodchild, J., "Conjugates of Oligonucleotides and Modified Oligonucleotides: A Review of Their Synthesis and Properties", *Bioconjugate Chemistry*, vol. 1, No. 3, pp. 165-187 (May/Jun. 1990).

Goring, D.R. et al., "In Situ Detection of β-Galactosidase in Lenses of Transgenic Mice with a γ-Crystallin/*lacZ* Gene", *Science*, vol. 235, pp. 456-458 (Jan. 23, 1987).

Graham, F.L. et al., "A New Technique for the Assay of Infectivity of Human Adenovirus 5 DNA", *Virology*, vol. 52, No. 2, pp. 456-467 (Apr. 1973).

Halbert, C. et al., "The E7 Gene of Human Papillomavirus Type 16 Is Sufficient for Immortalization of Human Epithelial Cells", *Journal of Virology*, vol. 65, No. 1, pp. 473-478 (Jan. 1991).

Harris, P. et al., "Polycystic Kidney Disease I: Identification and Analysis of the Primary Defect", *Journal of the American Society of Nephrology*, 6:1125-1133 (1995).

Hess, B. et al., "Cooperation of Glycolytic Enzyme", *Advances in Enzyme Regulation*, vol. 7, pp. 149-167 (1968).

Hiebert, S. et al., "The interaction of RB with E2F coincides with an inhibition of the transcriptional activity of E2F", *Genes & Development*, vol. 6, No. 2, pp. 177-185 (Feb. 1992).

Hiebert, S. et al., "E2F-1:DP-1 Induces p53 and Overrides Survival Factors to Trigger Apoptosis," *Molecular and Cellular Biology*, vol. 15, No. 12, pp. 6864-6874 (Dec. 1995).

Holland, M. et al., "Isolation and Identification of Yeast Messenger Ribonucleic Acids Coding for Enolase, Glyceraldehyde-3-phosphate Dehydrogenase, and Phosphoglycerate Kinase", *Biochemistry*, vol. 17, No. 23, pp. 4900-4907 (Nov. 14, 1978).

Hoogenboom, H. et al., "By-passing Immunisation Human Antibodies from Synthetic Repertoires of Germline $V_H$ Gene Segments Rearranged In Vitro", *J. Mol. Biol.*, vol. 227, No. 2, pp. 381-388 (Sep. 20, 1992).

Hopp, T. et al., "A Short Polypeptide Marker Sequence Useful for Recombinant Protein Identification and Purification", *Bio/Technology*, vol. 6, pp. 1204-1210 (Oct. 1988).

Hsiao, C. et al., High-frequency transformation of yeast by plasmids containing the cloned yeast *ARAG4* gene, *Proc. Natl. Acad. Sci. USA*, vol. 76, No. 8, pp. 3829-3833 (Aug. 1979).

Hugget, A. et al., "Development of Resistance to the Growth Inhibitory Effects of Transforming Growth Factor $\beta_1$ During the Spontaneous Transformation of Rat Liver Epithelial Cells", *Cancer Research*, vol. 51, No. 21, pp. 5929-5936 (Nov. 1, 1991).

Hunter, W.M. et al., "Preparation of Iodine-131 Labeled Human Growth Hormone of High Specific Activity", *Nature*, vol. 194, No. 4827, pp. 495-496 (May 5, 1962).

Iyer, R. et al., "3*H*-1,2-Benzodithiole-3-one 1,1-Dioxide as an Improved Sulfurizing Reagent in the Solid-Phase Synthesis of Oligodeoxyribonucleoside Phosphorothioates", *J. Am. Chem. Soc*, vol. 112, No. 3, pp. 1253-1254 (Jan. 31, 1990).

Iyer, R. et al., "The Automated Synthesis of Sulfur-Containing Oligodeoxyribonucleotides Using 3*H*-1,2-Benzodithiol-3-one 1,1-Dioxide as a Sulfur-Transfer Reagent", *The Journal of Organic Chemistry*, vol. 55, No. 15, pp. 4693-4699 (Jul. 20, 1990).

Jones, E., "Proteinase Mutants of *Saccharomyces cerevisiae*", *Genetics*, vol. 85, pp. 23-33 (Jan. 1977).

Jones, P. et al., "Replacing the complementarity-determining regions in a human antibody with those from a mouse", *Nature*, vol. 321, No. 6069, pp. 522-525 (May 29-Jun. 4, 1986).

Keown, W. et al., "[41] Methods for Introducing DNA into Mammalian Cells", *Methods in Enzymology*, vol. 185, pp. 527-537 (1990).

Kingsman, A. et al., "Replication in *Saccharomyces cerevisae* of Plasmid pBR313 Carrying DNA from the Yeast *trip1* Region" *Gene*, vol. 7, pp. 141-152 (1979).

Kohler, G. et al., "Continuous cultures of fused cells secreting antibody of predefined specificity", *Nature*, vol. 256, pp. 495-497 (Aug. 7, 1975).

Kozak, M., "Context Effects and Inefficient Initiation at Non-AUG Codons in Eucaryotic Cell-Free Translation Systems", *Molecular and Cellular Biology*, vol. 9, No. 11, pp. 5073-5080 (Nov. 1989).

La Thangue, N.B., "E2F and the molecular mechanisms of early cell-cycle control", *Biochemical Society Transactions*, vol. 24, No. 1, pp. 54-59 (Feb. 1996).

Lazar, E. et al., "Transforming Growth Factor $\propto$ Mutation of Aspartic Acid 47 and Leucine 48 Results in Different Biological Activities", *Molecular and Cellular Biology*, 8(3):1247-1252 (Mar. 1988).

Lee, W. et al., "Human Retinoblastoma Susceptibility Gene: Cloning, Identification, and Sequence", *Science*, vol. 235, pp. 1394-1399 (Feb. 20, 1987).

Li, E. et al., "Targeted Mutation of the DNA Methyltransferase Gene Results in Embryonic Lethality", *Cell*, vol. 69, No. 6, pp. 915-926 (Jun. 12, 1992).

Linsley, P. et al., "CTLA-4 Is a Second Receeptor for the B Cell Activation Antigen B7", *The Journal of Experimental Medicine*, vol. 174, pp. 561-569 (Sep. 1991).

Lutz-Freyermuth, C. et al., "Quantitative determination that one of two potential RNA-binding domains of the A protein component of the U1 small nuclear ribonucleoprotein complex binds with high affinity to stem-loop II of UI RNA", *Proc. Natl. Acad. Sci. USA*, vol. 87, No. 16, pp. 6393-6397 (Aug. 1990).

Mansour, S. et al., "Disruption of the proto-oncogene *int*-2 in mouse embryo-derived stem cells: a general strategy for targeting mutations to non-selectable genes", *Nature*, vol. 336, No. 6197, pp. 348-352 (Nov. 24, 1988).

Mantei, N. et al., "Rabbit β-globin mRNA production in mouse L cells transformed with cloned rabbit β-globin chromosomal DNA", *Nature*, vol. 281, pp. 40-46 (Sep. 6, 1979).

Marks, J., et al., "By-passing Immunization Human Antibodies from V-gene Libraries Displayed on Phage", *J. Mol. Biol.*, vol. 222, No. 3, pp. 581-597 Dec. 5, 1991.

Marra et al., vf65309.rl Barstead MPLRB1 Mus musculus cDNA clone 848680 5, *Database Embl-EMESTI*, Entry/Acc No. AA575702 (Sep. 11, 1997).

Marra, M. et al., Genbank Sequence Database, Accession No. AA57572 and MPSRCH search report, 2002, us-09-637-746-1.rst, p. 10, us-09-637-746-7.rst, pp. 8-9, us-09-637-746-9.rst, p. 8.

Martin, G., "GAP Domains Responsible for Ras p21-Dependent Inhibition of Muscarinic Atrial K⁺ Channel Currents", *Science*, vol. 255, pp. 192-194 (Jan. 1992).

Martin, S. et al., "Protease Activation during Apoptosis: Death by a Thousand Cuts?", *Cell*, vol. 82, No. 3, pp. 349-352 (Aug. 11, 1995).

Mather, J., "Establishment and Characterization of Two Distinct Mouse Testicular Epithelial Cell Lines", *Biology of Reproduction*, vol. 23, No. 1, pp. 243-252 (Aug. 1980).

Merrifield, R.B., "Solid Phase Peptide Synthesis. I. The Synthesis of a Tetrapeptide", *Journal of the American Chemical Society*, vol. 85, pp. 2149-2154 (Jul. 20, 1963).

Miller, A. et al., "Design of Retrovirus Vectors for Transfer and Expression of the Human β-Globin Gene", *Journal of Virology*, vol. 62, No. 11, pp. 4337-4345 (Nov. 1988).

Milstein, C. et al., "Hybrid hybridomas and their use in immunohistochemistry", *Nature*, vol. 305, No. 5934, pp. 537-540 (Oct. 6, 1983).

MPSRCH search report, 2002, us-09-637-746-1.rni, p. 3.

Moran, E., "DNA tumor virus transforming proteins and the cell cycle", *Current Opinion in Genetics and Development*, vol. 3, No. 1, pp. 63-70 (1993).

Munson, P. et al., "Ligand: A Versatile Computerized Approach for Characterization of Ligand-Binding Systems", *Analytical Biochemistry*, vol. 107, pp. 220-239 (1980).

Nevins, J., "E2F: A Link Between the Rb Tumor Suppressor Protein and Viral Oncoproteins", *Science*, vol. 258, pp. 424-429 (Oct. 16, 1992).

Negishi, E. et al., "Organozirconium Compounds in Organic Synthessi", *Journal of Synthetic Organic Chemistry*, No. 1, pp. 1-19 (Jan. 1988).

Nygren, H., "Conjugation of Horseradish Peroxidate to Fab Fragments with Different Homobifunctional and Heterobifunctional Cross-Linking Reagents", *The Journal of Histochemistry and Cytochemistry*, vol. 30, No. 5, pp. 407-412 (1982).

Osborne, T. et al., "5' End of HMG CoA Reductase Gene Contains Sequences Responsible for Cholesterol-Mediated Inhibition of Transcription", *Cell*, vol. 42, No. 1, pp. 203-212 (Aug. 1985).

Paborsky, L. et al., "Mammalian cell transient expression of tissue factor for the production of antigen", *Protein Engineering*, vol. 3, No. 6, pp. 547-553 (May 1990).

Padgett, R. et al., "Genetic and Biochemical Analysis of TGFβ Signal Transduction", *Cytokine & Growth Factor Reviews*, vol. 8, No. 1, pp. 1-9 (Mar. 1997).

Pain, D. et al., "Preparation of Protein A-Peroxidase Monoconjugate Using a Heterobifunctional Reagent, and its Use in Enzyme Immunoassays", *Journal of Immunological Methods*, vol. 40, No. 2, pp. 219-230 (1981).

Presta, L., "Antibody engineering", *Current Opinion in Structural Biology*, vol. 2 No. 4, pp. 593-596 (1992).

Price, J. et al., "Lineage analysis in the vertebrate nervous system by retrovirus-mediated gene transfer", *Proc. Natl. Acad. Sci USA*, vol. 84, pp. 156-160 (Jan. 1987).

Reynisdottir, I. et al., "Kip/Cip and Ink4 Cdk inhibitors cooperate to induce cell cycle arrest in response to TGF-β", *Genes & Development*, vol. 9, No. 15, pp. 1831-1845 (Aug. 1, 1995).

Riechmann, L. et al., "Reshaping human antibodies for therapy", *Nature*, vol. 332, No. 6162, pp. 323-327 (Mar. 24, 1988).

Shaw, C. et al., "A general method for the transfer of cloned genes to plant cells", *Gene*, vol. 23, No. 3, pp. 315-330 (Sep. 1983).

Skinner, R. et al., "Use of the Glu-Glu-Phe C-terminal Epitope for Rapid Purification of the Catalytic Domain of Normal and Mutant ras GTPase-Activating Proteins", *The Journal of Biological Chemistry*, vol. 266, No. 22, p. 14163-14166 (Aug. 5, 1991).

Slack R. et al., "Cells Differentiating into Neuroectoderm Undergo Apoptosis in the Absence of Functional Retinoblastoma Family Proteins", *The Journal of Cell Biology*, vol. 129, No. 3, p. 779-788 (May 1995).

Slansky, J.E. et al., "Introduction to the E2F Family: Protein Structure and Gene Regulation", *Current Topics in Microbiology and Immunology*, vol. 208, pp. 1-30 (1996).

Smith, K. et al., "Interaction of Mouse Adenovirus Type 1 Early Region 1A Protein with Cellular Proteins pRb and p107", *Virology*, vol. 224, No. 1, pp. 184-197 (Oct. 1, 1996).

Sporn, M. et al. Eds., "Peptide Growth Factors and Their Receptors 1", Table of Contents, pp. X-XXV, date? reviewed but cannot be published.

Stinchcomb, D.T. et al., "Isolation and characterization of a yeast chromosomal replicator", *Nature*, vol. 282, No. 5734, pp. 39-43 (Nov. 1, 1979).

Suresh, M.R. et al., "Bispecific Monoclonal Antibodies from Hybrid Hybridomas", *Methods in Enzymology*, vol. 121, pp. 210-228 (1986).

Tao, M. et al., "Studies of Aglycoslated Chimeric Mouse-Human IgG: Role of Carbohydrate in the Structure and Effector Functions Mediated by the Human IgG Constant Region", *The Journal of Immunology*, 143(8:2595-2601 (Oct. 15, 1989).

Taya Y., "RB kinases and RB-binding proteins: new points of view", *TIBS*, vol. 22, pp. 14-17 (Jan. 1997).

Thomas, K. et al., "Site-Directed Mutagenesis by Gene Targeting in Mouse Embryo-Derived Stem Cells", *Cell*, vol. 51, No. 3, pp. 503-512 (Nov. 5, 1987).

Thomas, P., "Hybridization of denatured RNA and small DNA fragments transferred to nitrocellulose", *Proc. Natl. Acad. Sci USA*, vol. 77, No. 9, pp. 5201-5205 (Sep. 1980).

Traunecker, A. et al., "Bispecific single chain molecules (Janusins) target cytotoxic lymphocytes on HIV infected cells", *The EMBO Journal*, vol. 10, No. 12, pp. 3655-3659 (Dec. 1991).

Tschumper, G. et al., "Sequence of a yeast DNA fragment containing a chromosomal replicator and the *TRP1* gene", *Gene*, vol. 10, pp. 157-166 (1980).

Urlaub, G. et al., "Isolation of Chinese hamster cell mutants deficient in dihydrofolate reductase activity", *Proc. Natl. Acad. Sci USA*, vol. 77, No. 7, pp. 4216-4220 (Jul. 1980).

van Solingen, P et al., "Fusion of Yeast Spheroplasts", *Journal of Bacteriology*, vol. 130, No. 2, pp. 946-947 (May 1977).

Verhoeyen, M. et al., "Reshaping Human Antibodies: Grafting an Antilysozyme Activity", *Science*, vol. 239, pp. 1534-1536 (Mar. 25, 1988).

Wang, J., "Retinoblastoma protein in growth suppression and death protection", *Current Opinion in Genetics & Development*, vol. 7, No. 1, pp. 39-45 (Feb. 1997).

Weinberg, R., "Tumor Supressor Genes", *Science*, vol. 254, pp. 1138-1146 (Nov. 22, 1991).

Wells, J. et al., "Cassette mutagenesis: an efficient method for generation of multiple mutations at defined sites", *Gene*, vol. 34, Nos. 2 and 3, pp. 315-323 (1985).

Wells, J.A. et al., "Importance of hydrogen-bond formation in stabilizing the transition state of subtilisin", *Phil. Trans. R. Soc. Land.*, vol. 317, No. 1540, pp. 415-423 (Apr. 30, 1986).

White, E., "Life, death, and the pursuit of apoptosis", *Genes & Development*, vol. 10, No. 1, pp. 1-15 (Jan. 1, 1996).

Whyte, P. et al., "Association between an oncogene and anti-oncogene: the adenovirus E1A proteins bind to the retinoblastoma gene product", *Nature*, vol. 334, No. 6178, pp. 124-129 (Jul. 14, 1988).

Woitach, J. et al., "A retinoblastoma-binding protein that affects cell-cycle control and confers transforming ability", *Nature Genetics*, vol. 19, No. 4, pp. 371-374 (Aug. 1998).

Woitach, et al., Database GenEmbl on GenCore Version 4.5, Accession No. AF025819 (Sep. 17, 1997).

Woitach et al., Database GenEmbl on GenCore Version 4.5, Accession No. AF039564 (Dec. 22, 1997).

Zerfass, K. et al., "Cell cycle-dependent disruption of E2F-p107 complexes by human papillomavirus type 16 E7", *Journal of General Virology*, vol. 76, Part 7, pp. 1815-1820 (1995).

Zoller, M. et al., "Oligonucleotide-directed mutagenesis using M13-derived vectors: an efficient and general procedure for the production of point mutations in any fragment of DNA", *Nucleic Acids Research*, vol. 10, No. 20, pp. 6487-6500 (Oct. 25, 1982).

Zwicker, J. et al., "Cell Cycle Regulation of E2F Site Occupation in Vivo", *Science*, vol. 271, No. 5253, pp. 1595-1597 (Mar. 15, 1996).

\* cited by examiner

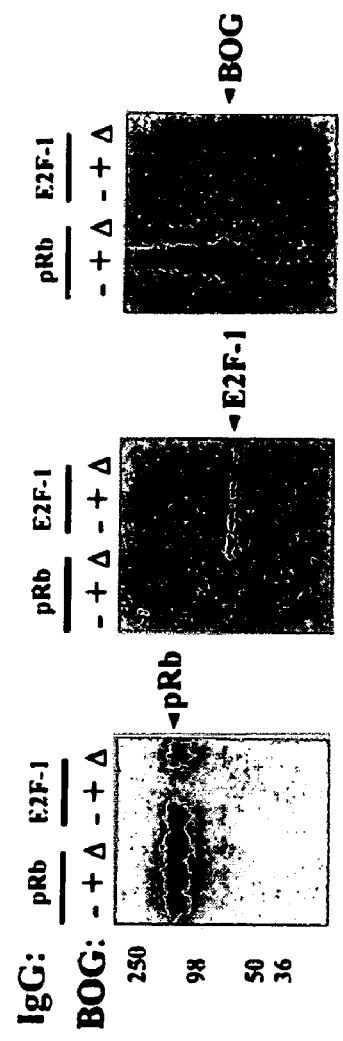
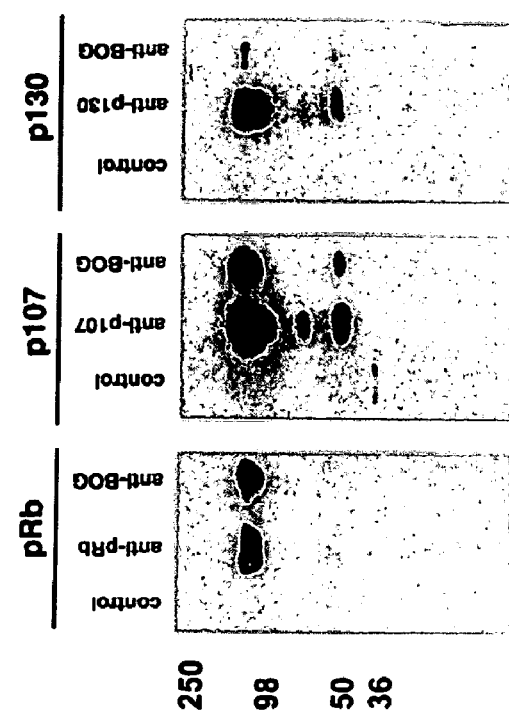
FIG. 2(C)
FIG. 2(D)

FIG. 5

BLAST SEARCH RESULTS

| | Name | Genbank number | Probality P(N) |
|---|---|---|---|
| 1 | Stratagene mouse melanoma cDNA clone 66379 | AA125075 (mq63h10.r1) | 1.5 e-150 |
| 2 | Life Tech mouse embryo cDNA 10 5dpc clone 557151 | AA111519 (me51h08.r1) | 1.5 e-146 |
| 3 | Soares mouse 3NbMS cDNA clone 622827 | AA184284 (mc33b02.r1) | 2.0 e-126 |
| 4 | Stratagene mouse embryonic carcinomaRA cDNA clone 535882 | AA105466 (mm92c06.r1) | 1.0 e-120 |
| 5 | WATMI Homosapiens cDNA clone 50l115 | N22688 (EST50l115) | 1.4 e-90 |

FIG. 9
FIG. 9(A)
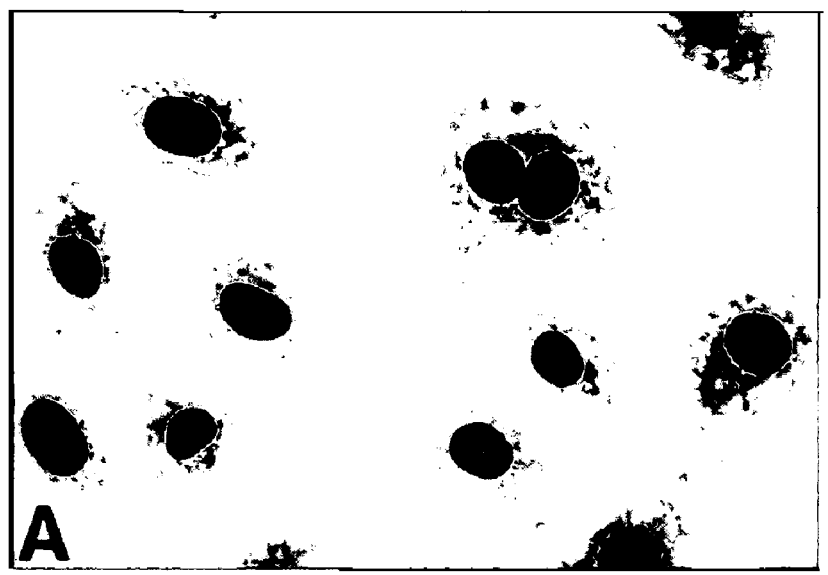
FIG. 9(B)
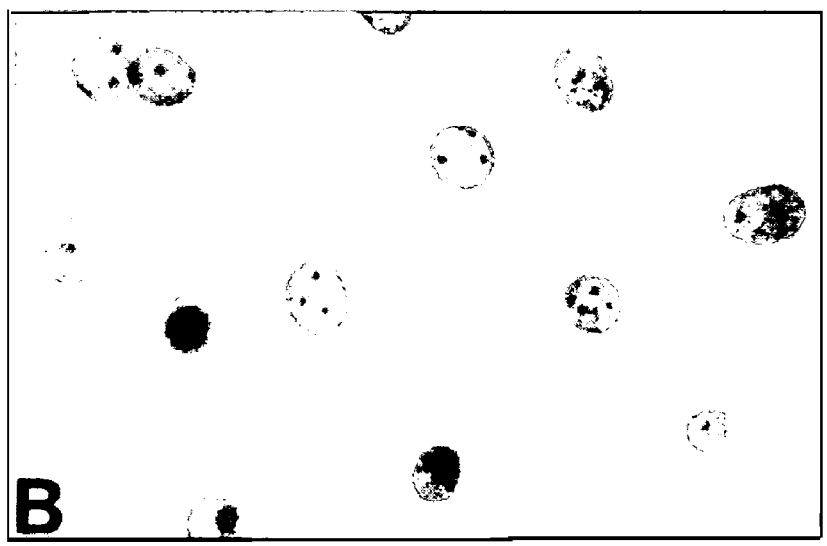

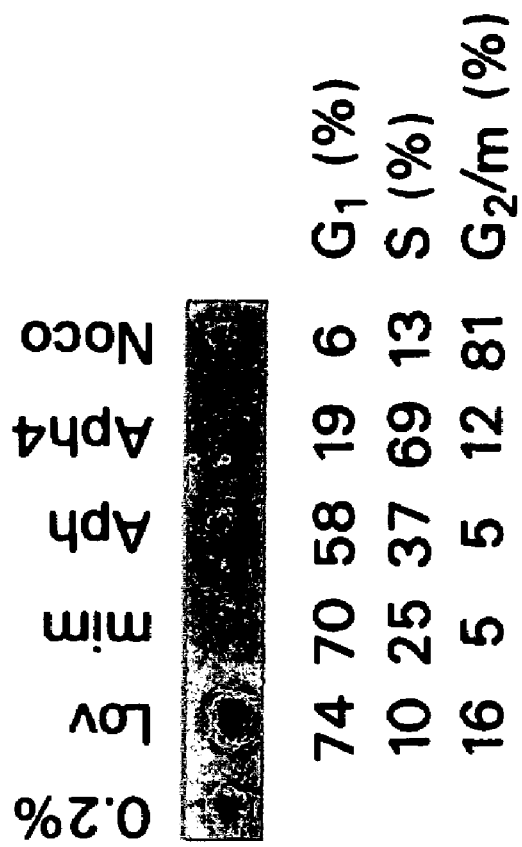
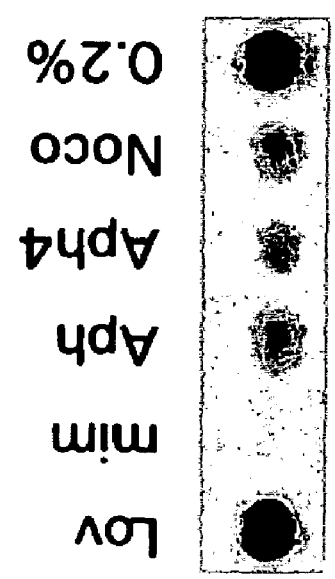
FIG. 10(A) B5T
FIG. 10(B) RLE

FIG. 13A

Sequence

RLHEXRT-3

```
00001    CAGAGCCCTGAAAGGTTGTTGCATGAGCCCGTGAAAGTGGAGTTTCAGTG
                      <------- NF-W1    (16.00  2.0000)
                      <------- NF-W2    (16.00  2.0000)
                           <---- Zeste   (12.00  2.0000)
                           <---- Zeste   (12.00  2.0000)
                                 ------------> BAF1   (10.00  0.8333)

00051    GTAGTGGATAGCATAGGACACTGGAGACACAGTTCATGTCCAGCATTCAT
            <------- C/EBP    (13.00  1.6250)
            <------- C/EBP    (13.00  1.6250)
            <------- C/EBP    (13.00  1.6250)
            <------- C/EBP    (13.00  1.6250)
             ----> NF-E       (10.00  2.0000)
                 -----> GR    (12.00  2.0000)
                      ----> ADR1    (10.00  2.0000)
                         <----- GR     (12.00  2.0000)
                             ----------> CBF (2)   (16.00  1.6000)
                             ----------> SRF       (16.00  1.6000)
                             <-------- Pit-1a     (14.00  2.0000)
00101    GGAGTGGGAGCAGAGAGTTCCCTGAAGCTCACTGGCTAGTATTCTTGCTA
            <----- GR    (10.00  2.0000)
                             --------> AGP/EBP    (10.00  1.1111)
                             --------> C/EBP      (11.00  1.2222)
                             --------> C/EBP      (11.00  1.2222)
                             --------> C/EBP      (11.00  1.2222)
                             --------> C/EBP      (11.00  1.2222)
                             --------> C/EBP      (11.00  1.2222)
                             --------> LAP        (10.00  1.1111)
                             --------> NF-IL6     (10.00  1.1111)
                             --------> NF-IL6beta (10.00  1.1111)
                             <--------- CP2       (10.00  0.9091)
                                 -----> CPIA      (14.00  2.0000)
```

FIG. 13B

```
                                              -----> CPIB       (14.00 2.0000)
                                              <----- ACF        (14.00 2.0000)
00151     AACCAATGAGCTCCAAATTCACAGATCTTGTCGCAAAACCCAAATGTAAT
          ---------> C/EBP     (10.00 2.0000)
          ---------> CBF (1)   (10.00 2.0000)
          ---------> CBF (2)   (10.00 2.0000)
          ---------> CBF-A     (10.00 2.0000)
          ---------> CBF-B     (10.00 2.0000)
          ---------> CCAAT-binding factor    (10.00 2.0000)
          ---------> CDF       (10.00 2.0000)
          ---------> CRF       (10.00 2.0000)
          ---------> CTF       (10.00 2.0000)
          ---------> NF-Y      (10.00 2.0000)
          ---------> NF-Y'     (10.00 2.0000)
          <--------- alpha-CBF (10.00 2.0000)
          <--------- alpha-CP1 (10.00 2.0000)
          <--------- alpha-CP2a, alpha-CP2b  (10.00 2.0000)
          <--------- alpha-IRP (10.00 2.0000)
          <--------- CDP       (10.00 2.0000)
          <--------- CDP2      (10.00 2.0000)
          <--------- Clox      (10.00 2.0000)
          <--------- CP1       (10.00 2.0000)
          <--------- CP1       (10.00 2.0000)
          <--------- CP2       (10.00 2.0000)
          <--------- Cux       (10.00 2.0000)
          <--------- En        (16.00 1.6000)
          <--------- H1TF2     (10.00 2.0000)
          <--------- NF-1      (10.00 2.0000)
          <--------- NF-E      (10.00 2.0000)
          <--------- NF-E      (10.00 2.0000)
          <--------- SRF       (10.00 2.0000)
          <--------- TGGCA-binding protein   (10.00 2.0000)
                     -----------> HiNF-A    (12.00 1.0000)
                                 <---------- CP2       (10.00 0.9091)
                                     -----> IUF-1     (10.00 1.6667)
                                     -----------> HiNF-A    (12.00 1.0000)
                                         <-------- AGP/EBP   (10.00 1.1111)
                                         <-------- AP 3 (2)  (13.00 1.6250)
                                         <-------- IgPE-1    (16.00 2.0000)
                                         <-------- LAP       (10.00 1.1111)
                                         <-------- NF-IL6    (10.00 1.1111)
                                         <-------- NF-IL6beta (10.00 1.1111)
00201     GTGGAAATGAAGGAAAAGAAGACACCCAACACTGACTGAATATGGTGACA
          <-------------- HSF        (14.00 0.9333)
          <-------------- HSF        (14.00 0.9333)
          <-------------- HSF        (14.00 0.9333)
          <-------------- HSF1 (long)   (14.00 0.9333)
          <-------------- HSF1 (short)  (14.00 0.9333)
```

FIG. 13C

```
                <------------- HSF1      (14.00 0.9333)
                -----> c-Ets-2           (12.00 2.0000)
                <----- c-Ets-1 54        (11.00 1.8333)
                <----- c-Ets-1 68        (11.00 1.8333)
                <----- c-Ets-2 58-64     (11.00 1.8333)
                <----- PEA3              (11.00 1.8333)
                <----- PEA3              (11.00 1.8333)
                <----- PEA3              (11.00 1.8333)
                -----> GR                (12.00 2.0000)
                   <---- CACCC-binding factor  (10.00 2.0000)
                   <---- gammaCAC1       (10.00 2.0000)
                   <---- gammaCAC2       (10.00 2.0000)
                       --------> AP-1    (16.00 2.0000)
                       -----> GCN4       (12.00 2.0000)
                          ----------> delta factor  (12.00 1.0909)
                          ----------> YY1           (12.00 1.0909)
                              <----- myc-CF1       (10.00 1.6667)
                              -----> p300          (14.00 2.0000)
00251   CTCCCTTTTAATGCCAGCACTCAGGAGACAAAAAGCAGGCAGATCTTTTG
           ----> NF-1/L       (10.00 2.0000)
           -----> GCN4        (12.00 2.0000)
           <----- Zeste       (12.00 2.0000)
           <----- Zeste       (12.00 2.0000)
              ----> ADR1      (10.00 2.0000)
                 ----> LVc    (10.00 2.0000)
                    ----> Zeste   (10.00 2.0000)
                    ----> Zeste   (10.00 2.0000)
00301   TGAGTTCTAGGCCAGTCTGGTTTACATAGACAGCTCCAGGCCAGTAAGGG
           <----- GR          (12.00 2.0000)
                ---------> NF-IL-2A   (16.00 1.6000)
                ---------> Oct-1      (16.00 1.6000)
                ---------> Oct-2.1    (16.00 1.6000)
                <----------- VBP      (20.00 1.6667)
                   ----> NF-E        (10.00 2.0000)
                      <---- T-Ag     (10.00 2.0000)
                      ----------> E4BP4   (12.00 1.2000)
00351   GCTAGCTAATGAAACTGTCTTAAACAAATTAACCAACGTTCATTTGAAAA
           -----> IUF-1       (10.00 1.6667)
           <------- STE12     (16.00 2.0000)
              <---- NF-E      (10.00 2.0000)
                  <---------- Ftz    (18.00 1.6364)
                  ----------> HOXA5  (10.00 1.0000)
                     -----> c-Ets-2  (12.00 2.0000)
                        <---------- EcR     (11.00 1.0000)
                        -----> TFIID        (12.00 2.0000)
                           ---------> Hb    (20.00 2.0000)
00401   AAAATAAACCTTCCTTAAAGAAGTATTGGTACAACTAATAAAAAGATAAC
           ---------> AGP/EBP      (10.00 1.1111)
```

FIG. 13D

```
--------> c-Ets-1 54      (11.00 1.8333)
--------> c-Ets-1 68      (11.00 1.8333)
--------> c-Ets-2 58-64   (11.00 1.8333)
--------> LAP       (10.00 1.1111)
--------> NF-IL6    (10.00 1.1111)
--------> NF-IL6beta (10.00 1.1111)
--------> PEA3      (11.00 1.8333)
--------> PEA3      (11.00 1.8333)
--------> PEA3      (11.00 1.8333)
<-------- kappaY factor   (16.00 2.0000)
  <----- c-Ets-2    (12.00 2.0000)
          ----> alpha-CBF     (10.00 2.0000)
          ----> alpha-CP1     (10.00 2.0000)
          ----> alpha-CP2A, alpha-CP2b   (10.00 2.0000)
          ----> alpha-IRP     (10.00 2.0000)
          ----> CDP       (10.00 2.0000)
          ----> CDP2      (10.00 2.0000)
          ----> Clox      (10.00 2.0000)
          ----> CP1       (10.00 2.0000)
          ----> CP1       (10.00 2.0000)
          ----> CP2       (10.00 2.0000)
          ----> Cux       (10.00 2.0000)
          ----> H1TF2     (10.00 2.0000)
          ----> NF-1      (10.00 2.0000)
          ----> NF-E      (10.00 2.0000)
          ----> NF-E      (10.00 2.0000)
          ----> SRF       (10.00 2.0000)
          ----> TGGCA-binding protein   (10.00 2.0000)
          <---- C/EBP     (10.00 2.0000)
          <---- CBF (1)   (10.00 2.0000)
          <---- CBF (2)   (10.00 2.0000)
          <---- CBF-A     (10.00 2.0000)
          <---- CBF-B     (10.00 2.0000)
          <---- CCAAT-binding factor    (10.00 2.0000)
          <---- CDF       (10.00 2.0000)
          <---- CRF       (10.00 2.0000)
          <---- CTF       (10.00 2.0000)
          <---- NF-Y      (10.00 2.0000)
          <---- NF-Y'     (10.00 2.0000)
                --------> HOXA5    (10.00 1.0000)
                --------> Hb       (16.00 1.6000)
                    -----> GATA-1    (12.00 2.0000)
                    <----- GATA-1    (10.00 1.6667)
                    <----- GATA-1    (10.00 1.6667)
                    <----- GATA-1    (10.00 1.6667)
                    <----- GATA-2    (10.00 1.6667)
                    <----- GATA-2    (10.00 1.6667)
                    <----- GATA-2    (10.00 1.6667)
```

FIG. 13E

```
                                          <----- GATA-2    (12.00 2.0000)
                                          <----- GATA-3    (10.00 1.6667)
                                          <----- GATA-3    (10.00 1.6667)
                                          <----- GATA-3    (10.00 1.6667)
                                          <----- GATA-3    (10.00 1.6667)
                                          <----- GATA-3    (10.00 1.6667)
                                          <----- NF-E1b    (10.00 1.6667)
                                          <----- NF-E1c    (10.00 1.6667)
                                          ----> DBF-A      (10.00 2.0000)
                                          <---- GAL4       (10.00 2.0000)
                                          <---- TBP        (10.00 2.0000)
00451   ACATTATGAGCACGCTGTTGCCAGCACATAAGGGATGTGGAGTATGAGAA
                    ----> NF-1/L          (10.00 2.0000)
                         ----> GCR1       (10.00 2.0000)
                               -------> C/EBP   (14.00 1.7500)
                               -------> C/EBP   (14.00 1.7500)
                               -------> C/EBP   (14.00 1.7500)
                               -------> C/EBP   (14.00 1.7500)
                               -------> C/EBP   (14.00 1.7500)
00501   GCGTGGAAAAGGGGTAAATCAAAGATAATTAATATTTGATGGTAATTCAC
        <------ AGP/EBP    (13.00 1.8571)
             -----------> HiNF-A    (12.00 1.0000)
        <---------- Kr      (16.00 1.6000)
             <---- Pit-1a   (10.00 2.0000)
                  -----> GATA-1     (12.00 2.0000)
                  <----- GATA-1     (10.00 1.6667)
                  <----- GATA-1     (10.00 1.6667)
                  <----- GATA-1     (10.00 1.6667)
                  <----- GATA-2     (10.00 1.6667)
                  <----- GATA-2     (10.00 1.6667)
                  <----- GATA-2     (10.00 1.6667)
                  <----- GATA-2     (12.00 2.0000)
                  <----- GATA-3     (10.00 1.6667)
                  <----- GATA-3     (10.00 1.6667)
                  <----- GATA-3     (10.00 1.6667)
                  <----- GATA-3     (10.00 1.6667)
                  <----- GATA-3     (10.00 1.6667)
                  <----- NF-E1b     (10.00 1.6667)
                  <----- NF-E1c     (10.00 1.6667)
                  ---------> DBF-A    (10.00 2.0000)
                  ---------> HOXA5    (10.00 1.0000)
                  <---------- GAL4    (10.00 2.0000)
                  <---------- TBP     (10.00 2.0000)
                      <------ N-Oct-3   (12.00 1.7143)
                      <------ N-Oct-3   (12.00 1.7143)
                      <------ N-Oct-3   (12.00 1.7143)
00551   AGGTTTGAGTTTAGCTGCCTGTGCTTTAGCCAGAAAATGCGTAGGCCTGC
        ----> Zeste    (10.00 2.0000)
```

FIG. 13F

```
               ----> Zeste      (10.00 2.0000)
                       <---------- CP2      (11.00 1.0000)
                                        ---------> Ker1    (16.00 1.6000)
                                          <---- LVc       (10.00 2.0000)
00601    AGGTATCCAAGAACTACAATTCCCAGAAGTCCGCAGTGCAGGCTCTGGGC
             -----> GR       (12.00 2.0000)
                   --------> AGP/EBP    (13.00 1.8571)
                   --------> IL-6 RE-BP  (18.00 2.0000)
                   --------> IL-6 RE-BP  (18.00 2.0000)
                              <--------- Sp1     (16.00 1.6000)
                              ----> Sp1          (10.00 2.0000)
                              ----> LVc          (10.00 2.0000)
                              ----> GAL4         (10.00 2.0000)
                               ----> GR          (10.00 2.0000)
                                <---- T-Ag       (10.00 2.0000)
                                ------> GCF      (10.00 1.4286)
                                  <--------- Elk-1    (10.00 1.0000)
                                   <--------- c-Ets-1  (16.00 1.6000)
                                    <------- c-Ets-1 54  (12.00 1.5000)
                                    <------- c-Ets-1 68  (12.00 1.5000)
                                    <------- c-Ets-1     (12.00 1.5000)
                                    <------- PEA3    (12.00 1.5000)
                                    <------- PEA3    (12.00 1.5000)
                                    <------- PEA3    (12.00 1.5000)
                                    ---------> Bcd   (16.00 1.6000)
                                     <--------- E1A-F  (14.00 2.0000)
00651    CGGATGTAGTCTTGGTCTGAGAGCTGCTGGTCCAAGCTGGGCAAGGTCTC
          ----> GCR1    (10.00 2.0000)
            <---------- EFII    (18.00 1.6364)
                        <---- H4TF-2   (10.00 2.0000)
                         <--------- GCF    (10.00 1.0000)
                          <---- T-Ag     (10.00 2.0000)
                           <---- LF-A1    (10.00 2.0000)
                             <------ ELP    (14.00 2.0000)
                              <---- ADR1    (10.00 2.0000)
00701    CCACGTCTACATTC
```

CDNA ENCODING A GENE BOG (B5T OVER-EXPRESSED GENE) AND ITS PROTEIN PRODUCT

RELATED APPLICATIONS

This application is a divisional of application Ser. No. 09/637,746, filed Aug. 11, 2000, now U.S. Pat. No. 6,727,079 issued Apr. 27, 2004 which is a continuation of international application No. PCT/US99/04142, filed on Feb. 25, 1999, which claims priority to U.S. Ser. No. 60/075,922, filed Feb. 25, 1998 and to U.S. Ser. No. 60/079,567, filed Mar. 27, 1998, which applications are incorporated herein by reference.

STATEMENT OF RIGHTS TO INVENTION MADE UNDER FEDERALLY SPONSORED RESEARCH AND DEVELOPMENT

The work performed during the development of this application utilized support from the National Institutes of Health. The United States government has certain rights in the invention.

FIELD OF THE INVENTION

The present invention relates generally to the isolation and characterization of novel DNA and polypeptides, designated herein as "BOG".

BACKGROUND OF THE INVENTION

Many types of human cancer are now believed to be caused by an imbalance of growth regulators within a cell. A decrease in negative control growth regulators and/or their deactivation can cause a cancerous condition. Further, an increase in positive control growth regulators can also cause a cancerous condition.

Since the identification of the first tumor suppressor gene, much effort in cancer research has been focused on the identification of cellular proteins which interact with tumor suppressor proteins and their involvement in human cancer. Moreover, many types of human cancers are thought to develop via mechanisms which impair the function of tumor suppressor genes.

One of the most studied tumor suppressor genes is the retinoblastoma susceptibility gene (RB), whose gene product (pRb) has been shown to play a key role in the regulation of cell division. R. A. Weinberg, Science, 254:1138 (1991). pRb is a nuclear protein that acts as a cell cycle control checkpoint by inhibiting G1/S progression. In interphasic cells, pRb contributes to maintaining the quiescent state of the cell by repressing transcription of genes required for the cell cycle through interaction with transcription factors, such as E2F (see e.g. Hiebert et al., Genes Develop., 6, 177-185 (1992)). Upon entrance into the cell cycle, pRb is phosphorylated by cell cycle-dependent kinases (see e.g. Matsushime et al., Nature, 35, 295-300 (1992)) which is thought to permit its dissociation from transcription factors and, hence, the expression of genes required for progression through the cell cycle. The association of pRb with cell cycle regulators like cyclins and cell cycle-dependent kinases suggests a universal character to its function.

Deletion or inactivation of both RB alleles is an essential, rate-limiting step in the formation of retinoblastoma and osteosarcoma that arise within families that carry a mutated RB gene. RB inactivation is also found in other sarcomas, small cell carcinoma of the lung, and in carcinoma of the breast, prostate and bladder. The restriction of pRb's involvement in human cancer to a limited number of tumor types suggests that its hypothetical universal function is influenced by other gene products in a cell type-specific manner. Consistently, knock out of the RB gene in mice affects only specific cell types after several days of embryonic development (see e.g. Clarke et al., Nature, 359, 328-330 (1992)). The loss of this activity can induce cell transformation as evidenced by the reversion of the transformed phenotype in pRb cells after replacement of a functional pRb. Moreover, injection of the RB gene product, pRb, into G1 cells can block cell cycle progression. Thus the identification of factors that interfere with and/or control pRb function is critical for understanding both cell cycle control and oncogenesis.

A major advance in the search for pRb function was the finding that pRb is a target for oncogenic products of DNA tumor viruses. Initial studies demonstrated that the adenovirus E 1A protein forms a complex with Rb which is dependent on sequences in the E1A protein. P. Whyte, et al., Nature, 334:124 (1988). Certain transforming proteins such as SV40T and E7, which are derived from the transforming or tumor-associated subtypes of adenoviruses and human papilloma viruses (HPV) are also capable of binding to pRb, thereby blocking its normal function. All these viral oncoproteins interact with pRb through an LXCXE motif (where X is any amino acid). Interaction of these viral proteins with pRb appears to be an important aspect of their oncogenic potential in which an inactivation of pRb function is achieved, that is equivalent to a deletion or mutation of RB. Growth factors such as transforming growth factor-β1 (TGF-β1) also exert their cell cycle control via pRb. A. B. Roberts, et al., Peptide Growth Factors And Their Receptors, 421-427 (1990). The mechanism(s) by which TGF-β1 inhibits cellular proliferation involves an attenuation of phosphorylation of pRb at the G1/S transition of the cell cycle. See e.g. I. Reynisdottir, et al. Genes Dev., 9:1831 (1995).

The ability of several transforming proteins from human DNA tumor viruses to activate cell proliferation has been a useful tool for the identification of cellular factors involved in the regulation of the cell cycle. Negative regulators of cell growth may thus be effective targets for inactivation by these viral proteins, as it occurs with the product of the retinoblastoma gene. Adenovirus E1A, SV40 T antigen, and papillomarivus E7 are three exemplary viral proteins which have been found to bind to pRb. This binding is responsible for the release of transcription factors required for the expression of cell cycle genes (see e.g. Nevins, Science. 258, 424-429 (1992).

A conserved motif found in the three viral proteins allows for interaction and complex formation with pRb (Moran, Curr. Op. Gen. Dev., 3, 63-70 (1993)). In the case of the adenovirus E1A protein, this motif is located in the transforming domain 2, which is required for growth activation. The pRb-related product p107 also binds in this region. Domain 2 is also the site of interaction of an additional E1A-binding protein, p130. This has led to the suggestion that p130 has a structural relationship to pRb and p107 (Moran, Curr. Op. Gen. Dev., 3, 63-70 (1993)).

The viral oncoprotein-binding domain in pRb, p107 and p130 is a conserved region termed the "pocket region" (see e.g. Ewin et al., Cell, 66, 1155-1164 (1991)), and it is thought to play a primary role in the function of these proteins. The pocket is structurally formed by two regions A and B, which are conserved in pRb, p107 and p130 and separated by nonconserved spacers of different sizes in pRb, p107 and p130.

In addition to its interaction with viral oncoproteins, pRb is known to bind at least two dozen cellular proteins. J. Wang, *Curr Opin Gen. Dev*, 7:39 (1997); Y. Taya, et al., *Trend Biochem. Sci.*, 22:14 (1997). Included in these is the transcriptional factor E2F-1 which is required for the transcription of certain cellular genes that participate in growth control and DNA synthesis (see e.g. W. B. La Thangue, et al., *Biochem. Soc. Trans.*, 24:54 (1996). It is now clear that E2F is composed of a family of closely related proteins, E2F-1 to -5, and a set of partner proteins belonging to the DP family of transcriptional factors (see e.g. J. E. Slansky, et al., *Curr. Top. Microbiol. Immunol.*, 208:1 (1996). E2F binds preferentially to the hypophosphorylated form of pRb and to several Rb related proteins, including p107 and p130. E2F can be dissociated from pRb and related protein complexes by two mechanisms: hyperphosphoylation of pRb or by the competitive binding with viral proteins. Treatment of cells with TGF-β1 results in the accumulation of pRb in the hypophosphorylated form. Hypophosphorylated pRb binds E2F-1 thus blocking the growth promoting activity of free E2F-1. However, co-expression of viral pRb binding proteins can reverse the TGF-β1 mediated arrest of cell growth presumably by displacing E2F-1 from pRb. K. Smith, et al. *Virology*, 224:184 (1996); K. Zerfass. *J. Gen. Virol.* 76:1815 (1995). Thus, hypophosphorylated pRb binds E2F-1 thereby blocking E2F-1 growth promoting activity whereas phosphorylation of pRb or complexing with viral oncoproteins releases E2F from pRb and leads to transcriptional activation of growth promoting genes.

The association of pRb with transcription factors, such as E2F, occurs by interactions at the pocket region and, recently, p107 has also been shown to exert such a binding profile. Moreover, the pocket region is found mutated in several human cancers where a lack of function of the pRb protein is thought to be involved in the acquisition of the transformed phenotype.

There is a need for identification and characterization of new cellular genes encoding proteins which interact with pRb and which may be involved in the regulation of cell growth. The isolation and characterization of genes encoding proteins which interact with pRb are particularly useful in studying mechanisms of cell proliferation and the means to modulate such activity.

SUMMARY OF THE INVENTION

Applicants have identified nucleotide sequences that encode a novel polypeptide, designated in the present application as "BOG" (B5T Over-expressed Gene), which exhibits a number of characteristics which make it a useful tool for studying cell cycle control and oncogenesis. BOG is a previously undescribed gene whose product binds the pRb tumor suppressor and is involved in regulating cellular growth. As BOG is shown to bind pRb, a factor known to regulate cellular growth and development, it is a prototype for molecules that function as endogenous regulators of cellular growth. As such, this novel protein has a variety of applications in the identification, characterization and regulation of activities associated with cellular regulation as well as processes associated with oncogenesis.

BOG is over-expressed in a number transformed rat liver epithelial (RLE) cell lines resistant to the growth inhibitor effect of TGF-β1 as well as in primary liver tumors. Over-expression of BOG in non-transformed TGF-β1 sensitive PLE cell lines can confer resistance to the growth inhibitory effect of TGF-β1. Furthermore, continuous over-expression of BOG in normal RLE cells typically leads to rapid transformation and the transformed cells can form hepatoblastoma-like tumors when transplanted into nude mice. Incubation of BOG over-expressing cells with BOG antisense oligonucleotides can restore sensitivity to TGF-β. Moreover, in vivo. BOG typically binds to pRb to form complex that does not contain E2F-1 and, in vitro. BOG can displace E2F-1 from E2F-1/pRb complexes. It is believed that BOG may be important in the transformation process, due in part, to the capacity of BOG to confer resistance to the growth inhibitory effects of TGF-β1 through interaction with pRb and the subsequent displacement of E2F-1.

In one embodiment, the invention provides an isolated nucleic acid molecule includes DNA which includes nucleotides which encode a BOG polypeptide. For example, the isolated nucleic acid can include DNA encoding BOG polypeptide having amino acid residues 1 to 173 of Tables 1, 5 or 7 or is complementary to such encoding nucleic acid sequence, and remains stably bound to it under at least moderate, and optionally, under high stringency conditions. In another embodiment, the invention provides a vector comprising a gene encoding a BOG polypeptide. A host cell comprising such a vector is also provided. By way of example, the host cells may be *E. coli*, yeast or mammalian cells. A process for producing BOG polypeptides is further provided and comprises culturing host cells under conditions suitable for expression of BOG. If desired, the BOG may be recovered.

In one embodiment, the invention provides an isolated polypeptide comprising a BOG fragment, wherein the BOG fragment comprises a pRb binding motif and a casein kinase II phosphorylation motif. In a favored embodiment, the isolated polypeptide exhibits BOG like activity and, typically, is capable of binding pRb. In another embodiment, the invention provides isolated BOG polypeptide. In particular, the invention provides isolated native sequence BOG polypeptide, which in one embodiment, includes an amino acid sequence comprising residues 1 to 173 of Table 1. In a related embodiment, the invention provides chimeric molecules comprising BOG polypeptide fused to a heterologous polypeptide or amino acid sequence. An example of such a chimeric molecule is a factor which includes a BOG fused to a protein such as the maltose binding protein. In yet another embodiment, the invention provides a polypeptide capable of specifically binding a BOG polypeptide such as an antibody specific for a BOG polypeptide. Optionally, the antibody is a monoclonal antibody.

In other embodiments, the invention provides methods for using BOG-RELATED polypeptides and nucleic acids for studying and modulating mechanisms involved in cellular proliferation. In one embodiment, the invention provides a method of modulating cellular phenotype by controlling the level of BOG expression within the cell. In a more specific embodiment, the invention provides a method of generating a transformed-cellular phenotype by overexpressing BOG. Alternatively, the invention provides a method of reducing BOG expression via antisense oligonucleotides in order to effect a cellular phenotype such as TGF-β sensitivity. In a related embodiment, the invention provides methods for effecting the interaction between pRb and pRb binding proteins.

BRIEF DESCRIPTION OF THE DRAWINGS

FIG. 2(C) shows displacement of E2F-1 from pRb/E2F-1 complexes by BOG. pRb/E2F-1 complexes were immunoprecipitated with either anti-pRb or anti-E2F-1 antibodies. Immunoprecipitates were divided into two samples, and to one sample BOG (a 70 kDa chimeric protein containing BOG fused to the maltose binding protein) was added. The samples were reprecipitated with the same antibody, separated on a 10% SDS-PAGE gel, and the same blot analyzed by Western blot analysis using anti-Rb, anti-BOG and anti-E2F-1 antibodies.

FIG. 2(D) shows the interaction of retinoblastoma family members and BOG. Antibodies to pRb, p107, p130 and BOG were used to precipitate proteins from whole cell extracts phi 13. The immunoprecipitates were separated on a 10% SDS-PAGE gel and analyzed by Western blot analysis to demonstrate the presence of pRb, p107 and p130 in the complexes.

FIG. 5 shows the results of a BLAST search and sequence analysis showing that a Blast search revealed only matches with sequences in EST database. Search results were obtained by using the open reading frame of rat BOG cDNA. The non-coding region of rat and mouse BOG both contain a B-1 like repeat and homology searches with this region produce many matches. Only the open reading frame of the human BOG sequence is available. P(N) value calculated by BLASTN search program with default values (reference Altschul, S. F. et al.).

FIG. 9(A) shows that rat BOG is localized to the nucleus as shown by staining with polyclonal antibodies.

FIG. 9(B) shows that preincubating the anti-BOG polyclonal antibodies with BOG antigen inhibits nuclear staining.

FIGS. 10(A) and 10(B) show that the expression of BOG is cell cycle regulated. When RLE and B5T cells-were synchronized at various points in the cell cycle, both cell lines show a similar pattern of expression of BOG during the cell cycle, with peak expression being seen during late G1.

FIGS. 13(A)-13(F) shows the sequence and a TESS-String based search partial characterization of the murine 5' genomic BOG DNA sequence (SEQ ID NO: 11) located approximately 10 nucleotides upstream of the ATG initiation codon.

DETAILED DESCRIPTION OF THE PREFERRED EMBODIMIENTS

1. Definitions

Figure 1:
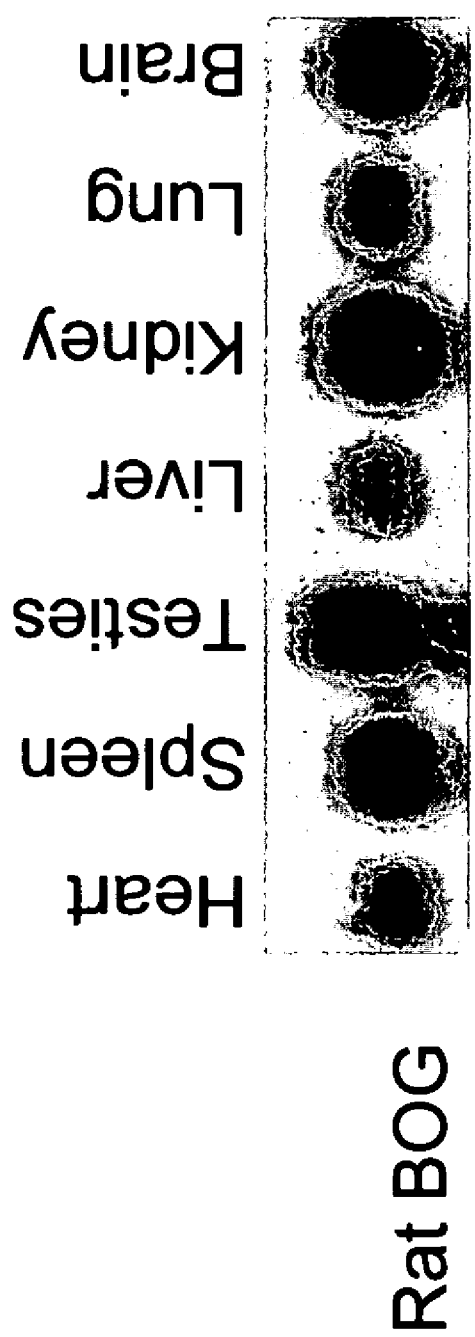
FIG. 1 shows a Northern blot analysis of BOG illustrating the normal expression pattern in various rat tissues.

The terms "BOG polypeptide" and "BOG" when used herein encompass native sequence BOG and BOG variants (which are further defined herein). The BOG may be isolated from a variety of sources, such as from human tissue types or from another source or prepared by recombinant or synthetic methods.

The BOG polypeptide, which may be a fragment of a native sequence, contains a retinoblastoma gene product (pRb) binding domain having the motif LXCXE. Typically, the BOG polypeptide also includes at least one casein kinase II phosphorylation motif that is typically located downstream (i.e. closer to the C-terminus of the polypeptide) from the pRb binding domain. Further, the BOG polypeptide may contain a second casein kinase II phosphorylation motif that is upstream from the pRb binding domain.

A "native sequence BOG" is a polypeptide having the same amino acid sequence as an BOG derived from nature. Such native sequence BOG can be isolated from nature or can be produced by recombinant or synthetic means. The term "native sequence BOG" specifically encompasses naturally-occurring variant forms (e.g., alternatively spliced forms) and naturally-occurring allelic variants of the BOG. In one embodiment of the invention, the native sequence BOG is a mature or full-length native sequence BOG polypeptide comprising amino acids 1 to 173 of Table 1. Alternatively, the BOG polypeptide comprises amino acid residues 1 to 173 of Tables 5 or 7.

"BOG variant" means a functionally active BOG as defined below having at least about 80% amino acid sequence identity with BOG, such as the BOG polypeptide having the deduced amino acid sequence shown in Tables 1, 5 or 7 for a full-length native sequence BOG. Such BOG variants include, for instance, BOG polypeptides wherein one or more amino acid residues are added, or deleted, at the N- or C-terminus of the sequence of Tables 1, 5 or 7. Ordinarily, a BOG variant will have at least about 80% or 85% amino acid sequence identity with native BOG sequences, more preferably at least about 90% amino acid sequence identity. Most preferably a BOG variant will have at least about 95% amino acid sequence identity with native BOG sequence of Tables 1, 5 or 7. As noted above, BOG variants include a pRb binding domain and typically, one or more casein kinase II sites. Functionally active BOG variants topically have at least about 50 and preferably at least about 100 amino acid residues.

"Percent (%) amino acid sequence identity" with respect to the BOG sequences identified herein is defined as the percentage of amino acid residues in a candidate sequence that are identical with the amino acid residues in the BOG sequence, after aligning the sequences in the same reading frame and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST software. Those skilled in the art can determine appropriate parameters for measuring alignment, including any algorithms needed to achieve maximal alignment over the full length of the sequences being compared.

"Percent (%) nucleic acid sequence identity" with respect to the BOG sequences identified herein is defined as the percentage of nucleotides in a candidate sequence that are identical with the nucleotides in the BOG sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared.

The term "epitope tagged" when used herein refers to a chimeric polypeptide comprising BOG, or a functional fragment thereof, fused to a "tag polypeptide". The tag polypeptide has enough residues to provide an epitope against which an antibody can be made, or which can be identified by some other agent, yet is short enough such that it does not interfere with activity of the BOG. The tag polypeptide preferably also is sufficiently unique so that the antibody does not substantially cross-react with other epitopes. Suitable tag polypeptides generally have at least six amino acid residues and usually between about 8 to about 50 amino acid residues (preferably, between about 10 to about 20 residues).

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified to a degree sufficient to obtain N-terminal or internal amino acid sequence by use of a spinning cup sequenator, or to homogeneity by SDS-PAGE under non-reducing or reducing conditions using Coomassie blue or silver stain. Isolated polypeptide includes polypeptide in situ within recombinant cells, since at least one component of the BOG natural environment will not be present. Ordinarily, however, isolated polypeptide will be prepared by at least one purification step (referred to herein as an "isolated and purified polypeptide").

An "isolated" BOG nucleic acid molecule is a nucleic acid molecule that is identified and separated from at least one contaminant nucleic acid molecule with which it is ordinarily associated in the natural source of the BOG nucleic acid. An isolated BOG nucleic acid molecule is other than in the form or setting in which it is found in nature.

Isolated BOG nucleic acid molecules therefore are distinguished from the BOG nucleic acid molecule as it exists in natural cells. However, an isolated BOG nucleic acid molecule includes BOG nucleic acid molecules contained in cells that ordinarily express BOG where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence: or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking may be accomplished by ligation at convenient restriction sites. If such sites do not exist, the synthetic oligonucleotide adaptors or linkers may be used in accordance with conventional practice. "Polynucleotide" and "nucleic acid" refer to single- or double-stranded molecules which may be DNA, comprised of the nucleotide bases A, T, C and G, or RNA, comprised of the bases A, U (substitutes for T), C, and G. The polynucleotide may represent a coding strand or its complement. Polynucleotide molecules may be identical in sequence to the sequence which is naturally occurring or may include alternative codons which encode the same amino acid as that which is found in the naturally occurring sequence (See. Lewin "Genes V" Oxford University Press Chapter 7, pp. 171-174 (1994)). Furthermore, polynucleotide molecules may include codons which represent conservative substitutions of amino acids as described. The polynucleotide may represent genomic DNA or cDNA.

"Polypeptide" refers to a molecule comprised of amino acids which correspond to those encoded by a polynucleotide sequence which is naturally occurring. The polypeptide may include conservative substitutions where the naturally occurring amino acid is replaced by one having similar properties, where such conservative substitutions do not alter the function of the polypeptide (See, Lewin "Genes V" Oxford University Press Chapter 1, pp.: 9-13 (1994)).

The term "antibody" is used in the broadest sense and specifically covers single anti-BOG monoclonal antibodies (including agonist, antagonist, and neutralizing antibodies) and anti-BOG antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

The term "manmmal" as used herein refers to any mammal classified as a mammal, including humans, cows, horses, dogs and cats. In a preferred embodiment of the invention, the mammal is a human.

II. Compositions and Methods of the Invention

A. BOG Nucleic Acids and Polypeptides

The present invention provides newly identified and isolated nucleotide sequences encoding polypeptides referred to in the present application as BOG. In particular, Applicants have identified and isolated genes and cDNA encoding BOG polypeptides, as disclosed in further detail in the Examples below. Using sequence homology searches. Applicants found that BOG (as shown in Tables 1, 5 and 7) contains the pRb binding motif LXCXE and shares certain amino acid sequence identity with pRb binding proteins including a number of viral oncoproteins (see Table 2). As shown in the Examples below, BOG polypeptide was found to bind pRb and to be able to displace other proteins complexed with pRb.

In addition to the full-length native sequence BOG and soluble forms of BOG described herein, it is contemplated that BOG variants can be prepared. BOG variants can be prepared by introducing appropriate nucleotide changes into the BOG nucleotide sequence, or by synthesis of the desired BOG polypeptide. Those skilled in the art will appreciate that amino acid changes may alter post-translational processes of the BOG, such as changing the number or position of glycosylation sites or altering the protein binding characteristics. Variations in the native full-length sequence BOG or in various domains of the BOG described herein, can be made, for example, using any of the techniques and guidelines for conservative and non-conservative mutations set forth, for instance, in U.S. Pat. No. 5,364,934. For example, amino acid substitutions at the H and/or D residues of the LHCDE motif are contemplated, such as conservative substitutions at one or both of these residues.

Variations may be a substitution, deletion or insertion of one or more codons encoding the BOG that results in a change in the amino acid sequence of the BOG as compared with the native sequence BOG. Optionally the variation is by substitution of at least one amino acid with any other amino acid in one or more of the domains of the BOG. Guidance in determining which amino acid residue may be inserted, substituted or deleted without adversely affecting the desired activity may be found by comparing the sequence of the BOG with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in any of the in vitro assays described in the Examples below.

In accordance with the practice of this invention. BOG molecules of the invention can have amino acid substitutions in the amino acid sequence shown in Tables 1, 5 and 7 (*Current Protocols In Molecular Biology*, Volume 1, Unit 8. Frederick M. Ausubul et al. eds.; 1995). Such substitutions result in BOG that retains the ability to bind pRb. These amino acid substitutions include, but are not necessarily limited to, amino acid substitutions known in the art as "conservative".

For example, it is a well-established principle of protein chemistry that certain amino acid substitutions, entitled "conservative amino acid substitutions," can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine and valine (V).

Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

Variations can be made using methods known in the art such as site-directed mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the BOG variant DNA. Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins*, (W.H. Freeman & Co., N.Y.); Chothia. *J. Mol. Biol.*, 150:1 (1976)]. If alanine substitution does not yield adequate amounts of variant, an isoteric amino acid can be used.

As discussed above, redundancy in the genetic code permits variation in BOG gene sequences. In particular, one skilled in the art will recognize specific codon preferences by a specific host species and can adapt the disclosed sequence as preferred for a desired host. For example, preferred codon sequences typically have rare codons (i.e., codons having a useage frequency of less than about 20% in known sequences of the desired host) replaced with higher frequency codons. Codon preferences for a specific organism may be calculated, for example, by utilizing codon usage tables available on the INTERNET at the following address: http://www.dna.affrc.go.jp/~nakamura/codon.html. Nucleotide sequences which have been optimized for a particular host species by replacing any codons having a useage frequency of less than about 20% are referred to herein as "codon optimized sequences."

Additional sequence modifications are known to enhance protein expression in a cellular host. These include elimination of sequences encoding spurious polyadenylation signals, exon/intron splice site signals, transposon-like repeats, and/or other such well-characterized sequences which may be deleterious to gene expression. The GC content of the sequence may be adjusted to levels average for a given cellular host, as calculated by reference to known genes expressed in the host cell. Where possible, the sequence may also be modified to avoid predicted hairpin secondary mRNA structures. Other useful modifications include the addition of a translational initiation consensus sequence at the start of the open reading frame, as described in Kozak, *Mol. Cell Biol.*, 9:5073-5080 (1989). Nucleotide sequences which have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequence."

B. Modifications of BOG

Covalent modifications of BOG are included within the scope of this invention. One type of covalent modification includes reacting targeted amino acid residues of the BOG with an organic derivatizing agent that is capable of reacting with selected side chains or the N- or C-terminal residues of the BOG. Derivatization with bifunctional agents is useful, for instance, for crosslinking BOG to a water-insoluble support matrix or surface for use in the method for purifying anti-BOG antibodies, and vice-versa. Commonly used crosslinking agents include, e.g., 1,1-bis(diazoacetyl)-2-phenylethane, glutaraldehyde, N-hydroxy-succinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate. In the alternative, BOG can be joined to a detectable label such as a radioactive isotope such as $I^{125}$ or $P^{32}$, an enzyme such as horseradish peroxidase or alkaline phosphatase, a fluorophore such as fluorescein isothiocyanate or a chromophore (*Current Protocols In Molecular Biology*, Volume 2, Units 10, 11 and 14, Frederick M. Ausubul et al. eds., 1995: *Molecular Cloning, A Laboratory Manual*, § 12, Tom Maniatis et al. eds., 2d ed. 1989).

Another type of covalent modification of the BOG polypeptide included within the scope of this invention comprises altering the native glycosylation pattern of the polypeptide. "Altering the native glycosylation pattern" is intended for purposes herein to mean deleting one or more carbohydrate moieties found in native sequence BOG, and/or adding one or more glycosylation sites that are not present in the native sequence BOG. Addition of glycosylation sites to the BOG polypeptide may be accomplished by altering the amino acid sequence. The alteration may be made, for example, by the addition of, or substitution by, one or more serine or threonine residues to the native sequence BOG (for O-linked glycosylation sites). The BOG amino acid sequence may optionally be altered through changes at the DNA level, particularly by mutating the DNA encoding the BOG polypeptide at preselected bases such that codons are generated that will translate into the desired amino acids. Another means of increasing the number of carbohydrate moieties on the BOG polypeptide is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259-306 (1981).

The BOG of the present invention may also be modified in a way to form a chimeric molecule comprising BOG fused to another, heterologous polypeptide or amino acid sequence. In one embodiment, such a chimeric molecule comprises a fusion of the BOG with a tag polypeptide which provides an epitope to which an anti-tag antibody can selectively bind. The epitope tag is generally placed at the amino- or carboxyl-terminus of the BOG. The presence of such epitope-tagged forms of the BOG can be detected using an antibody against the tag polypeptide. Also, provision of the epitope tag enables the BOG to be readily purified by affinity purification using an anti-tag antibody or another type of affinity matrix that binds to the epitope tag.

In an alternative embodiment, the chimeric molecule may comprise a fusion of the BOG with an immunoglobulin or a particular region of an immunoglobulin. The BOG may be fused any one of a variety of known fusion protein partners that are well known in the art such as maltose binding protein, LacZ, thioredoxin or an immunoglobulin constant region (*Current Protocols In Molecular Biology*, Volume 2. Unit 16, Frederick M. Ausubul et al. eds., 1995; Linsley, P. S., Brady, W., Urnes, M., Grosmaire, L., Damle, N., and Ledbetter, L. (1991) *J. Exp. Med.* 174, 561-566). In a preferred embodiment, this fusion partner is a non-BOG binding molecule so as to prevent difficulties associated with intramolecular interactions. For a bivalent form of the chimeric molecule, such a fusion could be to the Fc region of an IgG molecule. Other fusion proteins and tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto [Evan et al., Molecular and Cellular Biology, 5:3610-3616 (1985)]; and the Herpes Simplex virus glycoprotein D (gD) tag and its antibody [Paborsky et al., Protein Engineering, 3(6):547-553 (1990)]. Other tag polypeptides include the Flag-peptide [Hopp et al., BioTechnology, 6:1204-1210 (1988)]; the KT3 epitope peptide [Martin et al., Science, 255:192-194 (1992)]; an "-tubulin epitope peptide [Skinner et al., J. Biol. Chem., 266: 15163-15166 (1991)]; and the T7 gene 10 protein peptide tag [Lutz-Freyermuth et al., Proc. Natl. Acad. Sci. USA, 87:6393-6397 (1990)).

C. Preparation of BOG

The description below relates primarily to production of BOG by culturing cells transformed or transfected with a vector containing BOG nucleic acid. It is, of course, contemplated that alternative methods, which are well known in the art, may be employed to prepare BOG. For instance, the BOG sequence, or portions thereof, may be produced by direct peptide synthesis using solid-phase techniques [see, e.g., Stewart et al. Solid-Phase Peptide Synthesis. W. H. Freeman Co., San Francisco, Calif. (1969); Merrifield. J. Am. Chem. Soc., 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the BOG may be chemically synthesized separately and combined using chemical or enzymatic methods to produce the full-length BOG.

1. Isolation of DNA Encoding BOG

DNA encoding BOG may be obtained from a cDNA library prepared from tissue expressing a BOG mRNA. Accordingly, human BOG DNA can be conveniently obtained from a cDNA library prepared from human tissue. The BOG-encoding gene may also be obtained from a genomic library or by oligonucleotide synthesis. Libraries can be screened with probes (such as antibodies to the BOG or oligonucleotides of at least about 20-80 bases) designed to identify the gene of interest or the protein encoded by it.

Illustrative libraries include mouse kidney cDNA library (mouse kidney 5'-stretch cDNA. Clonetech laboratories, Inc.) and human liver cDNA library (human liver 5' stretch plus cDNA, Clonetech Laboratories, Inc.). Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding BOG is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency are provided in Sambrook et al. supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs which employs various algorithms to measure homology.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for BOG production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of transfection are known to the ordinarily skilled artisan, for example by using lipofectin, CaPO$_4$ or electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transformations have been described in U.S. Pat. No. 4,399,216. Transformations into yeast are typically carried out according to the method of Van Solingen et al., *J. Bact.,* 130:946 (1977) and Hsiao et al., *Proc. Natl. Acad. Sci. (USA.* 76:3829 (1979). However, other methods for introducing DNA into cells, such as by nuclear microinjection, electroporation, bacterial protoplast fusion with intact cells, or polycations. e.g., polybrene, polornithine, may also be used. For various techniques for transforming mammalian cells, see Keown et al., *Methods in Enzymology,* 185:527-537 (1990) and Mansour et al., *Nature,* 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example. Enterobacteriaceae such as *E. coli.* Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635).

Suitable host cells for the expression of glycosylated BOG are derived from multicellular organisms. Examples of invertebrate cells include insect cells such as Drosophila S2 and Spodoptera Sf9 cells. See e.g. *Current Protocols In Molecular Biology,* Volume I, Unit 16. Frederick M. Ausubul et al. eds., 1995. Examples of useful mammalian host cell lines include rat liver epithelial cells. Hugget, A. C. et. al. Supra. Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.,* 36:59 (1977)); Chinese hamster ovary cells/-DHFR(CHO, Urlaub and Chasin, *Proc. Natl. Acad. Sci. USA,* 77:4216 (1980)); mouse sertoli cells (TM4, Mather, *Biol. Reprod.,* 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding BOG may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general. DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The BOG may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the BOG DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* "-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2: plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins. e.g., ampicillin, neomycin, methotrexate, or tetracycline. (b) complement auxotrophic deficiencies, or (c) supply critical nutrients not available from complex media. e.g. the gene encoding D-alanine racemase for *Bacilli*.

An example of suitable selectable markers for mammalian cells are those that enable the identification of cells competent to take up the BOG nucleic acid, such as Neomycin, DHFR or thymidine kinase. An appropriate host cell when wild-type DHFR is employed is the CHO cell line deficient in DHFR activity, prepared and propagated as described by Urlaub et al., *Proc. Nail. Acad. Sci. USA,* 77:4216 (1980). A suitable selection gene for use in yeast is the trp1 gene present in the yeast plasmid YRp7 [Stinchcomb et al., *Nature.* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)]. Expression and cloning vectors usually contain a promoter operably linked to the BOG nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21-25 (1983)]. Promoters for use in bacterial systems also will contain a Shine-Dalgarno (S.D.) sequence operably linked to the DNA encoding BOG.

Examples of suitable promoting sequences for use with yeast hosts include the promoters for 3-phosphoglycerate kinase [Hitzeman et al., *J. Biol. Chem.,* 255:2073 (1980)] or other glycolytic enzymes [Hess et al., *J. Adv. Enzyme Reg.,* 7:149 (1968); Holland, *Biochemistry,* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73.657.

BOG transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovrirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the BOG by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, "-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the BOG coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding BOG. Still other methods, vectors, and host cells suitable for adaptation to the synthesis of BOG in recombinant vertebrate cell culture are described in Gething et al., *Nature*, 293:620-625 (1981); Mantei et al., *Nature*, 281:40-46 (1979); EP 117,060; and EP 117,058.

4. Detecting Gene Amplification/Expression

Gene amplification and/or expression may be measured in a sample directly, for example, by conventional Southern blotting. Northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence BOG polypeptide or against a synthetic peptide based on the DNA sequences provided herein or against exogenous sequence fused to BOG DNA and encoding a specific antibody epitope.

5. Purification of Polypeptide

Forms of BOG may be recovered from culture medium or from host cell lysates. Cells employed in expression of BOG can be disrupted by various physical or chemical means, such as freeze-thaw cycling, sonication, mechanical disruption, or cell lysing agents.

It may be desired to purify BOG from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the BOG. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular BOG produced.

D. Uses for BOG

Nucleotide sequences for their complement) encoding BOG have various applications in the art of molecular biology, including uses as hybridization probes, in chromosome and gene mapping and in the generation of anti-sense RNA and DNA. BOG nucleic acid will also be useful for the preparation of BOG polypeptides by the recombinant techniques described herein. BOG polypeptides have various applications in the art, including uses for evaluating factors that interact with and/or control pRb function as means for understanding both cell cycle control and oncogenesis. Moreover. BOG genes may introduced into cells to effect mechanisms mediated b TGF-β as well as processes involved in oncogenesis.

1. Screening Methods Utilizing BOG Nucleic Acids.

The full-length native sequence BOG (Tables 1, 5 and 7) gene, or portions thereof, may be used as hybridization probes for a cDNA library to isolate, for instance, still other genes (like those encoding naturally-occurring variants of BOG or BOG from other species) which have a desired sequence identity to the BOG sequences disclosed in Table 1, 5 and 7. Optionally, the length of the probes will be about 20 to about 500 bases. The hybridization probes may be derived from the nucleotide sequence or from genomic sequences including promoters, enhancer elements and introns of native sequence BOG. By way of example, a screening method will comprise isolating the coding region of the BOG gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the BOG gene of the present invention can be used to screen libraries of human cDNA, genomic DNA or mRNA to determine which members of such libraries the probe hybridizes to. Hybridization techniques are described in further detail in the Examples below.

Nucleotide sequences encoding a BOG can also be used to construct hybridization probes for mapping the gene which encodes that BOG and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

Screening assays can be designed to find lead compounds that mimic the biological activity of a native BOG or a ligand or receptor for BOG. Such screening assays will include assays amenable to high-throughput screening of chemical libraries, making them particularly suitable for identifying small molecule drug candidates. Small molecules contemplated include synthetic organic or inorganic compounds. The assay-s can be performed in a variety of formats, including protein-protein binding assays, biochemical screening assays, immunoassays and cell based assays, which are ell characterized in the art.

2. Modulation of BOG Protein Expression via BOG Antisense Oligonucleotides.

Antisense technology entails the administration of exogenous oligonucleotides which bind to a target polynucleotide located within the cells. The term "antisense" refers to the fact that such oligonucleotides are complementary to their intracellular targets, e.g. BOG. See for example, Jack Cohen, OLIGODEOXYNUCLEOTIDES, Antisense Inhibitors of Gene Expression, CRC Press, 1989; and Synthesis 1:1-5 (1988). The BOG antisense oligonucleotides of the present invention include derivatives such as S-oligonucleotides (phosphorothioate derivatives or S-oligos, see. Jack Cohen, supra) which exhibit enhanced cancer cell growth inhibitory action.

S-oligos (nucleoside phosphorothioates) are isoelectronic analogs of an oligonucleotide (O-oligo) in which a non-bridging oxygen atom of the phosphate group is replaced by a sulfur atom. The S-oligos of the present invention may be prepared by treatment of the corresponding O-oligos with 3H-1,2-benzodithiol ]-3-one-1,1-dioxide which is a sulfur transfer reagent. See Iyer, R. P. et al, J. Org. Chem. 55:4693-4698 (1990); and Iyer, R. P. et al., J. Am. Chem. Soc. 112:1253-1254 (1990), the disclosures of which are fully incorporated by reference herein.

The BOG antisense oligonucleotides of the present invention may be RNA or DNA which is complementary to and stably hybridizes with the first 100 N-terminal codons or last 100 C-terminal codons of the BOG genome or the corresponding mRNA. While absolute complementarity is not required, high degrees of complementarity are preferred. Use of an oligonucleotide complementary to this region allows for the selective hybridization to BOG mRNA and not to mRNA specifying other regulatory subunits of protein kinase. Preferably, the BOG antisense oligonucleotides of the present invention are a 15 to 30-mer fragment of the antisense DNA molecule having a sequence which hybridizes to BOG mRNA. Optionally, BOG antisense oligonucleotide is a 30-mer oligonucleotide which is complementary to a region in the first 10 N-terminal codons and last 10 C-terminal codons of BOG. Alternatively, the antisense molecules are modified to employ ribozymes in the inhibition of BOG expression. L. A. Couture & D. T. Stinchcomb; Trends Genet 12: 510-515 (1996).

In one embodiment, the BOG antisense oligonucleotide is coadministered with an agent which enhances the uptake of the antisense molecule by the cells. For example, the BOG antisense oligonucleotide may be combined with a lipophilic cationic compound which may be in the form of liposomes. The use of liposomes to introduce nucleotides into cells is taught, for example, in U.S. Pat. Nos. 4,897,355 and 4,394,448, the disclosures of which are incorporated by reference in their entirety. See also U.S. Pat. Nos. 4,235,871, 4,231,877, 4,224,179, 4,753,788, 4,673,567, 4,247,411, 4,814,270 for general methods of preparing liposomes comprising biological materials. Alternatively, the BOG antisense oligonucleotide may be combined with a lipophilic carrier such as any one of a number of sterols including cholesterol, cholate and deoxycholic acid.

In another embodiment, the BOG antisense oligonucleotide may be coadministered with a second agent that is effected by BOG expression. In one embodiment, this second agent is one or more isoforms of TGF-$\beta$. In a preferred embodiment, a combination of BOG antisense oligonucleotides and TGF-$\beta$1 are administered to cells which have reduced sensitivity to TGF-$\beta$ due to BOG overexpression. In this embodiment, a combination of these two molecules may be used to synergistically induce TGF-$\beta$1 mediated apoptosis. Methods pertaining to these embodiments are well known in the art. Zwicker et al., Science 271:1595-1597 (1996); Field et al., Cell 85: 549-561 (1996); Slack et al., J. Cell Bio. 129: 779-788 (1995); Hiebert et al., Mol Cell Biol 15: 6864-6874 (1995); White, E. Genes Dev 10: 1-15 (1996); Martin et al., Cell 82:349-352 (1995).

The antisense oligonucleotides of the present invention may be prepared according to any of the methods that are well known to those of ordinary, skill in the art. Preferably, the antisense oligonucleotides are prepared by solid phase synthesis. See. Goodchild. J., Bioconjugate Chemistry, 1:165-167 (1990), for a review of the chemical synthesis of oligonucleotides. Alternatively, the antisense oligonucleotides can be obtained from a number of companies which specialize in the custom synthesis of oligonucleotides.

3. Use of BOG Nucleic Acids in the Generation of Transgenic Animals.

Nucleic acids which encode BOG or its modified forms can also be used to generate either transgenic animals or "knock out" animals which, in turn, are useful in the development and screening of therapeutically useful reagents. A transgenic animal (e.g. a mouse or rat) is an animal having cells that contain a transgene, which transgene was introduced into the animal or an ancestor of the animal at a prenatal, e.g. an embryonic stage. A transgene is a DNA which is integrated into the genome of a cell from which a transgenic animal develops. In one embodiment, cDNA encoding BOG can be used to clone genomic DNA encoding BOG in accordance with established techniques and the genomic sequences used to generate transgenic animals that contain cells which express DNA encoding BOG. Methods for generating transgenic animals, particularly animals such as mice or rats, have become conventional in the art and are described, for example, in U.S. Pat. Nos. 4,736,866 and 4,870,009. Typically, particular cells would be targeted for BOG transgene incorporation with tissue-specific enhancers. Transgenic animals that include a copy of a transgene encoding BOG introduced into the germ line of the animal at an embryonic stage can be used to examine the effect of increased expression of DNA encoding BOG. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of BOG can be used to construct a BOG "knock out" animal which has a defective or altered gene encoding BOG as a result of homologous recombination between the endogenous gene encoding BOG and altered genomic DNA encoding BOG introduced into an embryonic cell of the animal. For example, cDNA encoding BOG can be used to clone genomic DNA encoding BOG in accordance with established techniques. A portion of the genomic DNA encoding BOG Can be deleted or replaced with another gene, such as a gene encoding a selectable marker which can be used to monitor integration. Typically, several kilobases of unaltered flanking DNA (both at the 5' and 3' ends) are included in the vector [see e.g. Thomas and Capecchi. Cell, 51:503 (1987) for a description of homologous recombination vectors]. The vector is introduced into an embryonic stem cell line (e.g. by electroporation) and cells in which the introduced DNA has homologously recombined with the endogenous DNA are selected [see e.g. Li et al., Cell, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson. ed. (IRL. Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the BOG polypeptide.

4. Use of BOG Upstream Control Sequences for Evaluating Neoplastic Processes

The genomic BOG control sequences of the present invention, whether positive, negative, or both, may be employed in numerous various combinations and organizations to assess the regulation of BOG. Moreover, in the context of multiple unit embodiments and/or in embodiments which incorporate both positive and negative control units, there is no requirement that such units be arranged in an adjacent head-to-head or head-to-tail construction in that the improved regulation capability of such multiple units is conferred virtually independent of the location of such multiple sequences with respect to each other. Moreover, there is no requirement that each unit comprise the same positive or negative element. All that is required is that such sequences be located upstream of and sufficiently proximal to a transcription initiation site.

To evaluate BOG regulatory elements in the context of heterologous genes, one simply obtains the structural gene and locates one or more of such control sequences upstream of a transcription initiation site. Additionally, as is known in the art, it is generally desirable to include TATA-box sequences upstream of and proximal to a transcription initiation site of the heterologous structural gene. Such sequences may be synthesized and inserted in the same manner as the novel control sequences. Alternatively, one may desire to simply employ the TATA sequences normally associated with the heterologous gene. In any event. TATA sequences are most desirably located between about 20 and 30 nucleotides upstream of transcription initiation.

Preferably the heterologous gene is a reporter gene which encodes an enzyme which produces calorimetric or fluorometric change in the host cell which is detectable by in situ analysis and which is a quantitative or semi-quantitative function of transcriptional activation. Exemplary enzymes include esterases, phosphatases, proteases (tissue plasminogen activator or urokinase) and other enzymes capable of being detected by activity which generates a chromophore or fluorophore as will be known to those skilled in the art. A preferred example is *E. coli* beta-galactosidase. This enzyme produces a color change upon cleavage of the indigogenic substrate indolyl-B-D-galactoside by cells bearing beta-galactosidase (see, e.g., Goring et al., Science, 235:456-458 (1987) and Price et al., Proc. Natl. Acad. Sci. U.S.A., 84:156-160 (1987)). Thus, this enzyme facilitates automatic plate reader analysis of BOG control sequence mediated expression directly in microtiter wells containing transformants treated with candidate activators. Also, since the endogenous beta-galactosidase activity in mammalian cells ordinarily is quite low, the analytic screening system using β-galactosidase is not hampered by host cell background.

Another class of reporter genes which confer detectable characteristics on a host cell are those which encode polypeptides, generally enzymes, which render their transformants resistant against toxins, e.g., the neo gene which protects host cells against toxic levels of the antibiotic G418; a gene encoding dihydrofolate reductase, which confers resistance to methotrexate, or the chloramphenicol acetyltransferase (CAT) gene (Osborne et al., Cell, 42:203-212 (1985)). Genes of this class are not preferred since the phenotype (resistance) does not provide a convenient or rapid quantitative output. Resistance to antibiotic or toxin requires days of culture to confirm, or complex assay procedures if other than a biological determination is to be made.

4. Use of BOG Polypeptides in Protein-Protein Interaction Studies.

The illustrative co-immunoprecipitation and Gal4 protein-protein interaction assays may useful in screening for compounds modulating BOG activity, or in screening for compounds altering BOG activity in a cell. For example, in proliferating cells, BOG participates with pRb in controlling the proliferative response of a cell to its environment. Those skilled in the art will understand that binding of a ligand at a molecular binding site can be modulated in a direct manner (e.g., by blocking the site), as ell as altered in an indirect manner (e.g. by conformational changes induced following binding of a second (different) ligand at a distant site). In this regard, it is likely that the binding site specificity of BOG for a particular pRb family member (or some other cellular control factor, as discussed below), can be completely altered (i.e. to bind a different ligand) by agents that bind at distant sites in the pRb polypeptide. A number of exemplary protocols which may be used in these studies are known in the art, see e.g. U.S. Pat. No. 5,625,031.

It is still further understood that, due to the significance of pRb in the cell cycle, innate regulator, mechanisms exist in cells for regulating their activity by binding to BOG or to complexes containing BOG. Such regulatory factors can include, at least: a) cofactors that bind to the complex and exert regulatory action by destabilizing or stabilizing the complex; b) agents that modulate or alter the activity of the complex by inducing conformational changes in the BOG polypeptides as they are bound together in the complex; c) enzymes that inactivate one or both members of the complex; and, d) cellular control factors (e.g., signal transduction second messengers, transcription regulatory factors, and the like) that bind pRb or pRb complexes and modulate or alter functional activity. Thus, polypeptides such as truncated BOG polypeptides can be constructed that control the activity of the BOG/pRb complexes in the cell by inhibiting or promoting the activities of such regulatory factors.

Those skilled in the art will recognize that the functional regions of pRb (including the A/B domains) and BOG are particularly attractive targets for three-dimensional molecular modeling and for the construction of mimetic compounds, e.g., organic chemicals constructed to mimic the three-dimensional interactions between BOG and pRb. See e.g. J. Wang, *Curr Opin Gen. Dev,* 7:39 (1997); Y. Taya, et al., *Trend Biochem. Sci.,* 22:14 (1997).

5. Use of BOG Containing Expression Vectors for Modulating Cellular Phenotype.

As discussed above. BOG genes can be incorporated into any standard cloning vector. The term "vector" is well understood in the art and is synonymous with the often-used phrase "cloning vehicle". A suitable vector is a non-chromosomal double-stranded DNA comprising an intact replicon such that the vector is replicated when placed within a unicellular organism.

Viral vectors include retroviruses, adenoviruses, herpes virus, papovirus, etc. Other suitable vectors include plasmids. Plasmids and retroviruses are generally preferred as vectors.

As discussed in Example 4, pBKCMV-BOG (pBKCMV purchased from Stratagene$^{tm}$) was constructed and contained the CMV promoter. This promoter is suitable for expression of the BOG genes in a wide variety of cells. However, the CMV promoter is not specifically required for transcription and expression of the BOG genes. Optionally, one may replace the CMV promoter with other knows promoters to improve the efficiency of transcription and expression in particular cells.

The promoter DNA can be amplified using PCR technology while concurrently providing restriction sites at the 5' and 3' ends of the promoter DNA. The amplified promoter DNA can then be inserted into a cloning vehicle (for example pBKCMV) using conventional endonucleases and known recombinant DNA technology. Cloning vectors containing the desired promoter upstream of the 5' end of BOG genes are constructed in this manner.

As discussed in Examples 4 and 5, it is possible to influence cellular phenotype using the BOG gene. In this context, cloning vectors containing an appropriate promoter and the BOG gene may be constructed using PCR technology in a manner analogous to the preparation of vectors containing exogenous genes as is well known in the art. Cloning vectors containing BOG genes are transfected into host cells using known transfection processes. Suitable transfection processes include lipofection, electroporation and retrovirus infection. When transfecting cells with BOG, the desired cells are isolated and cultured in suitable media.

Transfection of cells using lipofection may conducted according to standard lipofection procedures. See Felgner et al. 1987. Proc. Natl. Acad. Sci. (USA). 84:7413-7417. In general, liposome-mediated DNA transfection is accomplished by exposing 1-20 micrograms of plasmid DNA and commercially available liposomes (Bethesda Research Laboratories) in culture medium. The transfected cells are then repeated passaged in culture medium and the desired clones are isolated.

Retrovirus infection may also be accomplished using previously described procedures. See for example Miller et al. J. Virol. 62:4337-4345 and Halbert et al. J. Virol. 65:473-378, 1991. In general, plasmid DNA is transfected into a desired packaging cell line such as Psi-2 or other cell lines, using standard calcium phosphate precipitation. Viruses produced from the Psi-2 cells or equivalent cells are then used to infect an amphotropic packaging cell line, for example PA317. Viruses produced by the amphotropic packaging cell line are used to infect the desired host parent cells of the present invention.

Selection of clones with a modulated phenotype may be undertaken by a variety of protocols that are well known in the art (see e.g. U.S. Pat. No. 5,376,542). In such selections, the cells may be selected for their ability to respond to factors such as TGF-β. Alternatively cells can be selected by their ability to form colonies and grow in soft agar. Moreover, the cells can be selected by their ability to form tumors in animal models such as in nude mice. After transfection, the desired clones are selected by culturing in optimal media and repeated passaging. Generally, 10-20 passages are required to eliminate spurious cells and obtain pure clonal cells. Optimal media are selected according to the type of parent cell which is utilized. For lymphocytes, RPMI media is preferred; for fibroblasts, DMEM media is preferred; and for epithelial cells, a serum-free medium such as keratinocyte growth medium (KGM) or SFM (Gibco Company) is preferred.

Selected colonies are then tested to verify the presence of BOG DNA and the expression of BOG genes. Verification is confirmed by standard Southern hybridization techniques and immunoprecipitation to determine the presence or quantity of expressed BOG proteins.

6. Chromosomal Localization.

In Example 8, chromosomal localization of the human and murine BOG genes is described. Chromosomal localization was done by FISH analysis (Stokke, T. et al., Genomics 26: 134-137 (1995)). Murine BOG maps to chromosome 2 and in human to the syntenic region of chromosome 20.

In other embodiments the invention provides diagnostic assays for determining chromosomal rearrangement of BOG genes in a cell. The chromosomal location of BOG genes is conveniently determined in chromosomal smears by in situ hybridization with oligonucleotide probes or cDNA and the like. Translocation of a BOG gene, i.e. from a chromosomal location found in a normal cell to a location found in a transformed cell, may contribute to a phenotype of uncontrolled cell growth by removing normal transcription regulatory control of either gene expression of a BOG or RB polypeptide. In the case where the rearrangement induces over-expression the cell may acquire a malignant (i.e. uncontrolled) growth phenotype, and in the case where the rearrangement induces under-expression the cell may undergo premature senescence. Screening cellular samples from individuals for the potential of BOG chromosomal rearrangement may indicate a relative risk factor for the possibility of developing cancer.

E. Anti-BOG Antibodies

The present invention further provides anti-BOG antibodies. Exemplary antibodies include polyclonal, monoclonal, humanized, bispecific, and heteroconjugate antibodies.

1. Polyclonal Antibodies

The BOG antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the BOG polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). Further, polyclonal antibodies may be generated commercially, for example by Genemed Synthesis, Inc. using art accepted methods.

2. Monoclonal Antibodies

The BOG antibodies may, alternatively, be monoclonal antibodies. Monoclonal antibodies may be prepared using hybridoma methods, such as those described by Kohler and Milstein. *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the BOG polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies. Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against BOG. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard. *Anal. Biochem.*, 107:220 (1980).

After the desired hybridoma cells are identified, the clones may be subcloned by limiting dilution procedures and grown by standard methods [Goding, supra]. Suitable culture media for this purpose include, for example. Dulbecco's Modified Eagle's Medium and RPMI-1640 medium. Alternatively, the hybridoma cells may be grown in vivo as ascites in a mammal. The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography. The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking. In vitro methods are also suitable for preparing monovalent antibodies. Digestion of antibodies to produce fragments thereof particularly. Fab fragments, can be accomplished using routine techniques known in the art.

3. Humanized Antibodies

The BOG antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.* 227:381 (1991); Marks et al. *J. Mol. Biol.*, 222:581 (1991)]. The techniques of Cole et al., and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86-95 (1991)].

4. Bispecific Antibodies

Bispecific antibodies are monoclonal, preferably human or humanized, antibodies that have binding specificities for at least two different antigens. In the present case, one of the binding specificities is for the BOG, the other one is for any other antigen, and preferably for a cell-surface protein or receptor or receptor subunit. Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.*, 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example. Suresh et al., *Methods in Enzymology*, 121:210 ((1986).

5. Heteroconjugate Antibodies

Heteroconjugate antibodies are also within the scope of the present invention.) Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373: EP 03089]. It is contemplated that the antibodies may be prepared in Vitro using known methods in synthetic protein chemists, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

F. Uses for BOG Antibodies

The BOG antibodies of the invention have various utilities. For example, BOG antibodies may be used in diagnostic assays for BOG, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982). In addition, BOG or antibodies which recognize BOG may be used in drug screening assays to identify compounds which act as BOG antagonists or agonists. Antibodies may also be useful therapeutically either alone, as agents which would act directly to interfere with the function of BOG or indirectly as targeting agents capable of delivering a toxin conjugated, for example, pseudomonas exotoxin or radioisotopes, thereto to a desired site.

BOG antibodies also are useful for the affinity purification of BOG from recombinant cell culture or natural sources. In this process, the antibodies against BOG are immobilized on a suitable support, such a Sephadex resin or filter paper, using methods well known in the art. The immobilized antibody then is contacted with a sample containing the BOG to be purified, and thereafter the support is washed with a suitable solvent that will remove substantially all the material in the sample except the BOG, which is bound to the immobilized antibody. Finally, the support is washed with another suitable solvent that will release the BOG from the antibody.

The following examples are offered for illustrative purposes only, and are not intended to limit the scope of the present invention in any way. All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, 10801 University Boulevard, Manassas, Va., USA.

Example 1

Isolation of Rat BOG cDNA and Determination of Tissue Expression

Figure 4A:
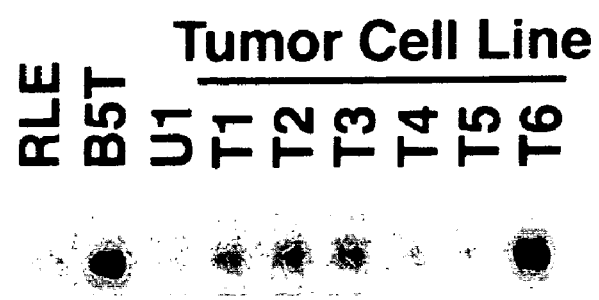
FIG. 4(A) shows increased expression of BOG correlates with transformation. Total RNA was isolated from several untransformed (RLE phi 13 and U1) and transformed (B5T and T1-6) RLE cell lines. (Cell lines: phi 13 nontransformed RLE cell line passage 22; B5T, a transformed clone from passage 36; U1=B7, a nontransformed RLE clone passage 36; T1=AFL-B8, T2=AFL-C2 and T3=AFL-D7 are aflatoxin-transformed RLE cell lines; T4=J2; a v-raf/v-myc transformed RLE cell line; T5=T2 and T6=F3611-3, v-raf-transformed RLE cell lines.) 20 μg of total RNA was analyzed by Northern blot analysis using the 1.9 kb BOG cDNA as a probe.

Loss of TGF-β1 induced growth inhibition is an early event during spontaneous transformation of RLE cells. A. C. Hugget, et al., *Cancer Res.*, 51:5929 (1991). This resistance to the growth inhibitory effects of TGF-β1 can clearly be caused by multiple factors. E. R. Barrack, *Prostate*, 31:61 (1997); R. W. Padgett, et al., *Cytokine Growth Factor Rev.*, 8:1 (1997); L. Attisano, et al., *Cytokine Growth Factor Rev.*, 7:327 (1996). However, we had observed a number of the transformed cell lines displaying resistance to the growth inhibitory effects of TGF-β1 that apparently had "normal" number of TGF-β receptors. A. C. Hugget, et al., *Cancer Res.*, 51:5929 (1991). These observations suggested a post-receptor disruption of the growth inhibitory signal(s) of TGF-β1. To search for endogenous genes which confer resistance to the grouch inhibitory effects of TGF-β1, and in turn may lead to cellular transformation, subtractive hybridization was done on two RLE cell lines that were sensitive (RLE phi 13) or insensitive (B5T) or TGF-β. A novel transcript. BOG (B5T Over-expressed Gene), was identified and shown to be over-expressed in the B5T, as well as several other transformed RLE lines which are resistant to the effects of TGF-β1 (FIG. 4A).

A 1897 bp cDNA clone % as obtained which encoded a protein of 173 amino acids with a predicted Mr~19,000 Daltons (Tables 1, 5 and 7). DNA homology searches of Genbank-revealed BOG to be a unique transcript. BOG mRNA was translated in vitro and the product analyzed by polyacrylamide gel electrophoresis, which confirmed the protein size as 19.3 KDa protein. We compared the deduced amino acid sequence of BOG with known proteins in the Swissprot data base. While BOG appeared to be a novel protein, it contained domains similar to other proteins. The deduced protein sequence contained a pRb-binding motif LXCXE (Table 1, double underlined) and two casein kinase II phosphorylation sites (Table 1, underline). Alignment of the pRb-binding motif in BOG protein with that in HPV 16 E7, SV40 large T antigen, adenovirus E1A and Rb-binding protein is shown in Table 2. In addition to the pRb-binding region. BOG and HPV16 E7 exhibited 29.6% identity and 7.1% similarity over the whole sequence BOG (Table 3). Expression of BOG in the rat was analyzed using a multi-tissue northern blot (FIG. 1). Transcript for BOG could be detected in all tissues but varied in expression levels, demonstrating the highest expression in the spleen, testis and kidney. The ubiquitous expression pattern suggests a general rather than cell specific function for BOG.

Protocols for the isolation of rat BOG cDNA. Poly(A)+ was isolated from RLE-13 and B5T cells by using oligo (dt) cellulose, as previously described (Bradley J E, Bishop G A, St John T, Frelinger J A (1988): Biotechniques 6:114-116. The cDNAs were synthesized using SuperScript reverse transcriptase (BRL) as recommended by the vendor; added with BstXI adaptor (InVitrogen) and used to produce RLE-13 and B5T cDNA libraries in pcDNAIneo.

For B5T cDNA enriched subtractive cDNA library construction, B5T and RLE-13 cDNAs were digested with HindIII+XbaI and BamHI+XhoI, respectively and subjected to agarose gel purification. Digested RLE-13 cDNA fragments (20 μg) were digested further with AluI-RsaI and dephosphorylated, then hybridized with HindIII+XbaI digested B5T cDNA fragments (0.4 μg). The hybridization mixture was used to construct the B5T cDNA enriched subtractive cDNA library in BluescriptM13 with HindIII-XbaI protruding termini. The enriched library was plated and single colonies were isolated. The plasmid from each clone/colony was sequenced, and novel sequences were used to screen a panel of rat tumor samples and synchronized cells.

The cDNA sequence of rat BOG was determined by double strand sequence analysis of a 1.9 kb clone. Sequencing of plasmids was performed using one of two kits; Dye Terminator Ready Reaction Kits-FS (cat# 402080) or Big-Dye Termninator Ready Reaction Kits (cat# 4303149), Perkin-Elmer Applied Biosystems. The reactions were purified using Centrisep Spin Columns (cat# CS-901), Princeton Separations. The samples were analyzed on a 377 ABI Prism DNA sequencer, Perkin-Elmer Applied Biosystems. The predicted amino acid sequence was derived using PCGENE and indicated below with single letter code.

Protocols for BOG Northern blot analysis. Poly (A)+ RNA was isolated and selected using oligo (dt) cellulose (Bradley J E, Bishop G A, St John T, Frelinger J A (1988), Biotechniques 6:114-116.), and 5 μg fractionated under denaturing conditions by electrophoresis through 1.2% agarose-formaldehyde gel, transferred to nitrocellulose and hybridized with a 500 bp fragment of BOG corresponding to the open reading frame. All blots were rehybridized with a probe to actin to ensure equal loading and integrity of the mRNA samples.

Example 2

Assessing BOG and pRb Interaction Using a Yeast Two-Hybrid System.

Figure 2A:
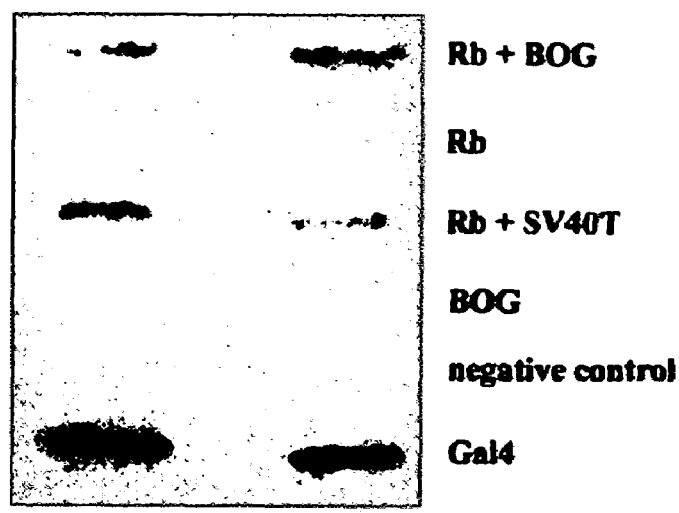
FIG. 2(A) shows the yeast two-hybrid system as used to demonstrate the interaction of Rb and BOG in vivo (Matchmaker Gal4 Two-hybrid System, Clontech). Vectors containing only BOG, Rb, or vector not containing insert were used as negative controls to demonstrate lack of growth on selective media and lack of β-galactosidase activity. SV40 large T was used as a positive control to demonstrate interaction with Rb. Growth rates and β-galactosidase activity for BOG and Rb were similar to those exhibited by SV40T and Rb.

As stated previously, BOG contains the LXCXE pRb-binding motif found in many of the Rb binding proteins. To test the interaction between BOG and pRb, we employed the yeast two-hybrid system. The appropriate plasmid constructs were sequentially transformed into yeast reporter strains GAL1 promoter activity was analyzed by growth on plates lacking histidine. CYC1 promoter activity also was analyzed by induction of lacZ by staining clones on X-gal containing media (FIG. 2A). As a positive control for both promoters SV40 large T antigen (pTD1) interaction with pRb (pGBT9/Rb) was used. The intensity of X-gal staining for Rb and BOG as compared to pRb and SV40 large T suggests that their degree of interaction is comparable.

Protocols involving the Gal4 two-hybrid system. The yeast two-hybrid system was used to demonstrate the interaction of Rb and BOG in vivo (Matchmaker Gal4 Two-hybrid System, Clontech). The complete open reading frame of BOG was cloned into pGAD424, and a fragment of Rb, the 1.9 kb BsmHI-SalI fragment of Rb from pASRB2 was cloned into pGBT9. All other plasmids, SV40T (pTD1) GAL4 (pCL1) were obtained from Clontech's two hybrid system. The plasmids were sequentially transformed into yeast strain HF7c and picked by growth on selective media. The appropriate clones were streaked onto filters and assayed for β-galactosidase activity. Yeast clones with plasmids containing only Rb, BOG, or both expression vectors without insert served as negative controls, while the interaction of SV40T and Rb, and wild type GAL4 served as positive controls. The yeast Matchmaker Gal4 Two-hybrid System (cat# K1605-1), Clontech Laboratories, Inc., contains the vectors pGAD424, pGBT9, pTD1 and pCL1.

Example 3

Figure 2B:
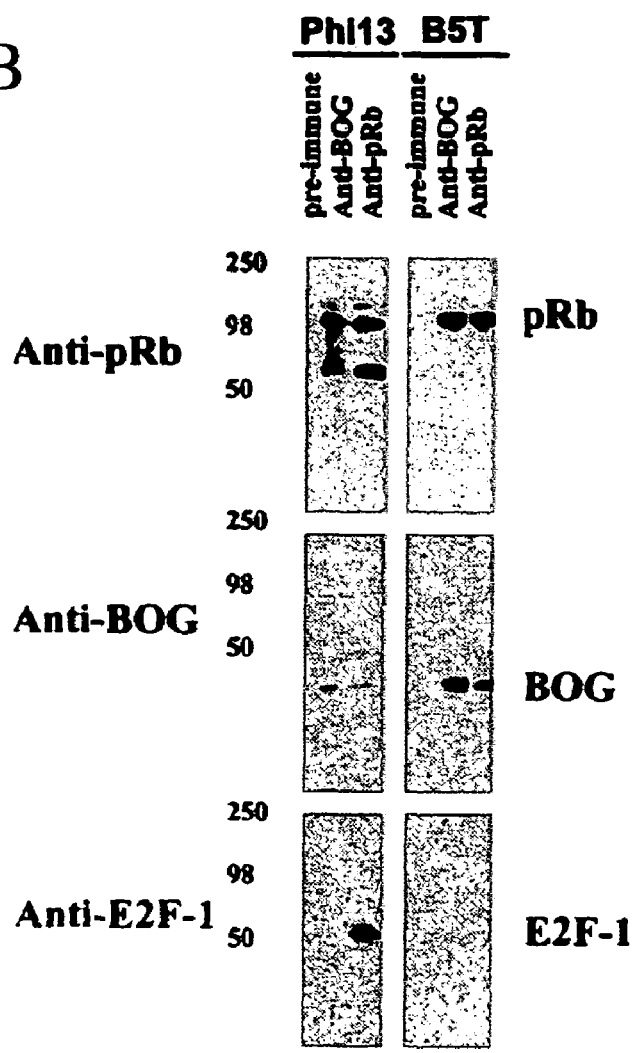
FIG. 2(B) shows co-immunoprecipitation from whole cell extracts of phi 13 and B5T cells were performed with anti-Rb, anti-BOG antibodies and nonspecific preimmune serum. Immunoprecipitates were separated on a 10% SDS-PAGE gel and analyzed by Western blot analysis. Anti-Rb, anti-BOG and anti-E2F-1 antibodies were used to examine the proteins present in the immunoprecipitated complexes.

Assessment of BOG, E2F-1 and pRb Interaction via Coimmunoprecipitation Studies. To confirm the interaction of pRb and BOG, whole cell lysates were subjected to co-immunoprecipitation with either anti-pRb, anti-E2F-1 or anti-BOG antibodies and analyzed by Western blot (FIG. 2B). From cells over-expressing BOG, pRb could be precipitated with both anti-BOG and anti-Rb. However when the blot is stripped and re-analyzed with anti-E2F-1. E2F-1 could be detected only in the samples precipitated with anti-Rb. This indicates that the pRb associated with BOG is not bound to E2F-1, suggesting that BOG competes and could displace E2F-1 from pRb. This model is supported by the analysis of the B5T cells which over-express BOG. When one compares the amount of pRb precipitated from RLE and B5T cells by anti-pRb antibodies, similar amounts of pRb are present in the whole cell extracts (FIG. 2B). However, in the presence of greater amounts of BOG as in the B5T cells, the amount of E2F-1 bound in the pRb complexes is dramatically reduced. An important implication of this observation is that overexpression of BOG may be needed to displace E2F-1 from pRb.

To test directly if BOG could displace E2F-1 from pRb/E2F-1 complexes, non-transformed RLE cells were treated with TGF-β1 for 24 hours to allow for synchronization of the cells in late G1, and the accumulation of Rb/E2F-1 complexes. The pRb/E2F-1 complexes were immunoprecipitated with either anti-Rb or anti-E2F-1 antibodies, and incubated with the fusion protein BOG-MBP. The lysates were precipitated again and analyzed by Western blot analysis (FIG. 2C). These results show clearly that BOG binds to pRb and can compete with and displace E2F-1 bound to pRb.

It has also been reported that viral genes that contain the LXCXE pRb binding consensus sequence can interact with the other retinoblastoma gene family members. P. Whyte, et al., *Nature*, 334:124 (1988); W. H. Lee, et al., *Science*, 235:1394 (1987); R. Bernards, et al., *Proc. Natl. Acad. Sci. USA*, 86:6474 (1989). Both p130 and p107 share homology to pRb, containing highly conserved domains including H1, H2 and the large pocket subdomains A and B. To evaluate if BOG also interacts with these proteins, whole cell lysates were prepared from RLE cells and co-immunoprecipitation experiments were performed with anti-BOG, anti-pRb, anti-p130 and anti-p107 antibodies. As illustrated in FIG. 2D, BOG is present in complexes with all the Rb family members. This suggests that overexpression of BOG may affect the regulation p107 and p130, as well as pRb. Changes in the regulation of p107 and p130 may be an important contributing factor in the rapid transformation seen in the RLE cell line, however, the specific effect of BOG overexpression on these Rb family members needs to be further investigated.

Protocols for the precipitation of BOG from whole cell extracts. Co-immunoprecipitation from whole cell extracts of phi 13 cells teas performed with anti-Rb 1F8 (Santa Cruz Biotechnology), anti-BOG antibodies and nonspecific preimmune serum.

Immunoprecipitates were separated on a 10% SDS-PAGE gel and analyzed by Western blot analysis using anti-Rb, anti-BOG and anti-E2F-1 antibodies (Santa Cruz Biotechnology). To assay the ability of BOG to displace E2F-1 from the pRb complex, a chimeric protein was constructed using the Protein and Purification System (New England Biolabs. Inc.). The pMAL-P2 vector used produced a protein in Which BOG is fused to the carboxy-terminal of the maltose binding protein (MBP). The chimeric protein was purified using an amylose resin and tested for its ability to precipitate pRb from whole cell lysates. Protein preparations capable of precipitating pRb were used for displacement experiments. The purified IMIBP without BOG did not precipitate any proteins from whole cell lysates under similar conditions. Displacement of E2F-1 from pRb/E2F-1 complexes by BOG were performed with RLE phi 13 cells treated with TGF-β1 (500 pmol) for 24 hours to maximize pRb/E2F-1 complex formation. Cells were harvested and whole cell extracts were immunoprecipitated with anti-Rb and anti-E2F-1 antibodies (Santa Cruz Biotechnology). Immunocomplexes were aliquoted into two factions, and to one fraction the chimeric BOG-MBP was added the second fraction served as a control and received only buffer. Both fractions were allowed to incubate for 1 hour. The mixtures were immunoprecipitated again the same antibodies as before. The immunoprecipitates were separated on a 10% SDS-PAGE gel and analyzed by Western blot analysis using anti-Rb, anti-BOG, and ($^{125}$I) anti-E2F-1 antibodies. Immunoprecipitation for p107 and p130 (anti-p107 C18 and anti-p130 C20; Santa Cruz Biotechnology) was performed on whole cell extracts of RLE phi 13.

For the experiments involving PAGE electrophoresis and Western blotting, SDS-PAGE and electro-transfer blotting was performed using XCell II Mini-Cell (Dual Slab) & Blot Module (cat# EI9002), Novex. Proteins were separated on 10% Tricine gels 1.0 mm/10 well (ca# EC6675) using the appropriate buffer systems; Tricine SDS running buffer (10×) (cat# LC1675) and Tricine Sample Buffer (2×) (cat# LC 1676), Novex. Gels were electro-transferred to pre-cut Nitrocellulose (cat# LC2001), Novex. In vitro translation was performed on the rat cDNA using TnT T7 quick Coupled Transcription/Translation System (cat# L1171), Promega.

Example 4

Evaluation of Cellular Phenotype as a Function of BOG Expression.

Figure 3A:
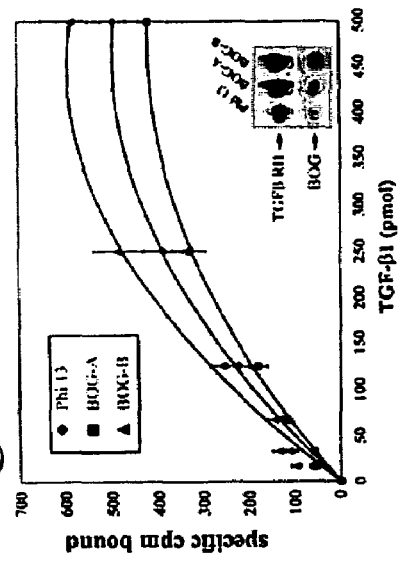
FIG. 3(A) shows colony formation of a heterogeneous population of transfected RLE and B7 cells expressing BOG. Two RLE cell lines, phi 13 and B7, which are untransformed and known to be sensitive to TGF-β were transfected with BOG or empty vector. After the cells were allowed to recover, they were cultured in the presence of TGF-β1 for 14 days. Most cells that contained the empty vector control did not grow or died during the two weeks in culture. Colonies grow in cells overexpressing BOG were stained with crystal violet.

Previous studies in our laboratory indicated that spontaneous transformation of RLE cells was accompanied by acquisition of resistance to TGF-β1 mediated growth inhibition and suggested that the resistance to TGF-β1 was an important and possibly essential step in the spontaneous transformation process. A. C. Hugget, et al. *Cancer Res.*, 51:5929 (1991). We reasoned that over-expression of BOG, acting by displacing E2F-1 from pRb might, at least in part, account for loss of TGF-β1 growth inhibition observed during spontaneous transformation of the RLE cells. To test this hypothesis constitutive over-expression of BOG was established in the non-transformed RLE and B7 cell lines. The cells transfected with either pcDNA-BOG or control plasmid pcDNA, were subjected to neomycin selection, and pools of neomycin-resistant RLE, RLE/BOG, B7 and B7/BOG cells were generated. The four pools were then cultured in the presence of 0.5 ng/ml TGF-β1. The presence of pcDNA-BOG plasmid in RLE/BOG and B7/BOG cells significantly decreased the sensitivity of these cells to growth inhibition by TGF-D growth (FIG. 3A).

We also compared the TGF-β1 sensitivity in single cell clones transfected with either control plasmid pBKCMV or with pBKCMV-BOG containing expression plasmid pBKCMV-BOG. Expression of BOG in these clones was 3 to 7.5 fold higher than in the TGF-β1 sensitive RLE cells (FIG. 3C inset). Over-expression of BOG did not significantly affect either the binding of TGF-β1 to the cell surface receptors of TGF β receptor II mRNA expression (FIG. 3C).

To address the possible linkage between over-expression of BOG and transformation further, we analyzed expression of BOG in various transformed and non-transformed cells lines derived from the RLE cells (FIG. 4A). Expression of BOG in non-transformed RLE (lane 1) and B7 cell lines U1 (lane 3) was very low, while higher expression levels were detected in all transformed cell lines except T5 (lane 8), a cell line transformed by v-raf. A. C. Hugget, et al., *Cancer Res.*, 51:5929 (1991). All the cell lines examined exhibited a similar doubling time, and since RNA was extracted from the cells during log phase growth, mitotic index alone can not account for the increased expression of BOG in the transformed cell lines.

Figure 4B:
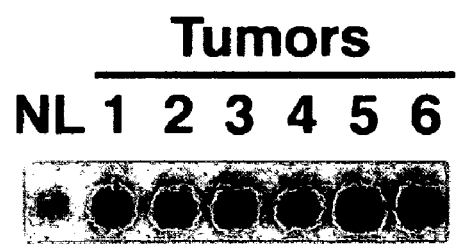
FIG. 4(B) shows BOG expression in rat liver tumors. Tumors were derived utilizing the Solt-Farber carcinogenesis protocol (17) and were analyzed by Northern blot analysis using the 1.9 kb BOG cDNA as a probe. A. B. Roberts, et al., *Peptide Growth Factors And Their Receptors*, 421-427 (1990)

However, since the T5 line, one of the more aggressive transformed RLE cell lines, did not demonstrate increased expression of BOG, suggesting the overexpression of BOG is not an absolute requirement for transformation of the RLE cells. To evaluate the relationship between BOG expression and transformation in vitro hepatocellular carcinomas were chemically induced in male rats. A. B. Roberts, et al., *In Peptide Growth Factors And Their Receptors*, 421-427 (1990). Six tumors were analyzed for BOG expression, and all displayed elevated expression as compared to normal rat liver tissue (FIG. 4B). It is important to restate here that one of the early events in the transformation process in the liver is loss of sensitivity of TGF-β. While the increased expression of BOG in the tumors may be due in part to the increased mitotic activity in the tumor, an increased expression of BOG in all the tumors may reflect the importance of BOG in the selection of the clonal phenotype that maintained a growth advantage during neoplastic development in the liver.

Figure 4C:
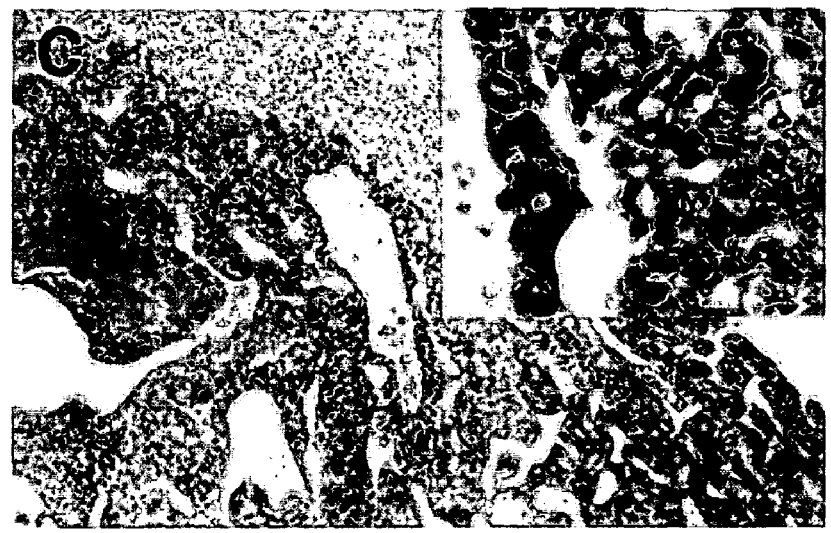
FIG. 4(C) shows tumors from nude mice derived from the BOG-A cell line. Paraffin embedded sections were stained with hematoxylin-eosin (H&E) for histological evaluation.
Figure 6B:
FIG. 6(B) is a multi-tissue blot analysis showing that rBOG is expressed ubiquitously in all tissues analyzed.
Figure 6A:
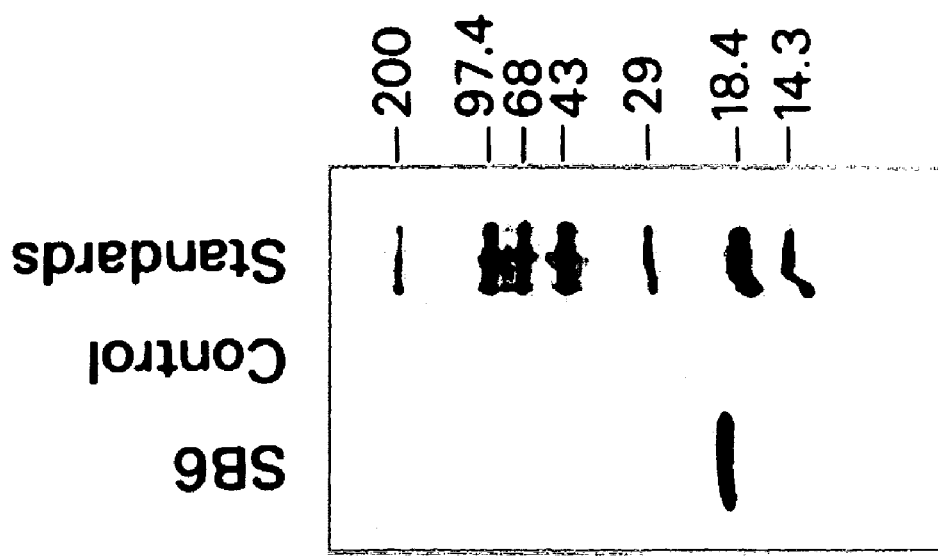
FIG. 6(A) shows in vitro translation data and Western Blot data characterizing BOG. In vitro translation of rBOG produces a 20 kDA protein and Western blot analysis identifies a protein of the same molecular weight.
Figure 7:
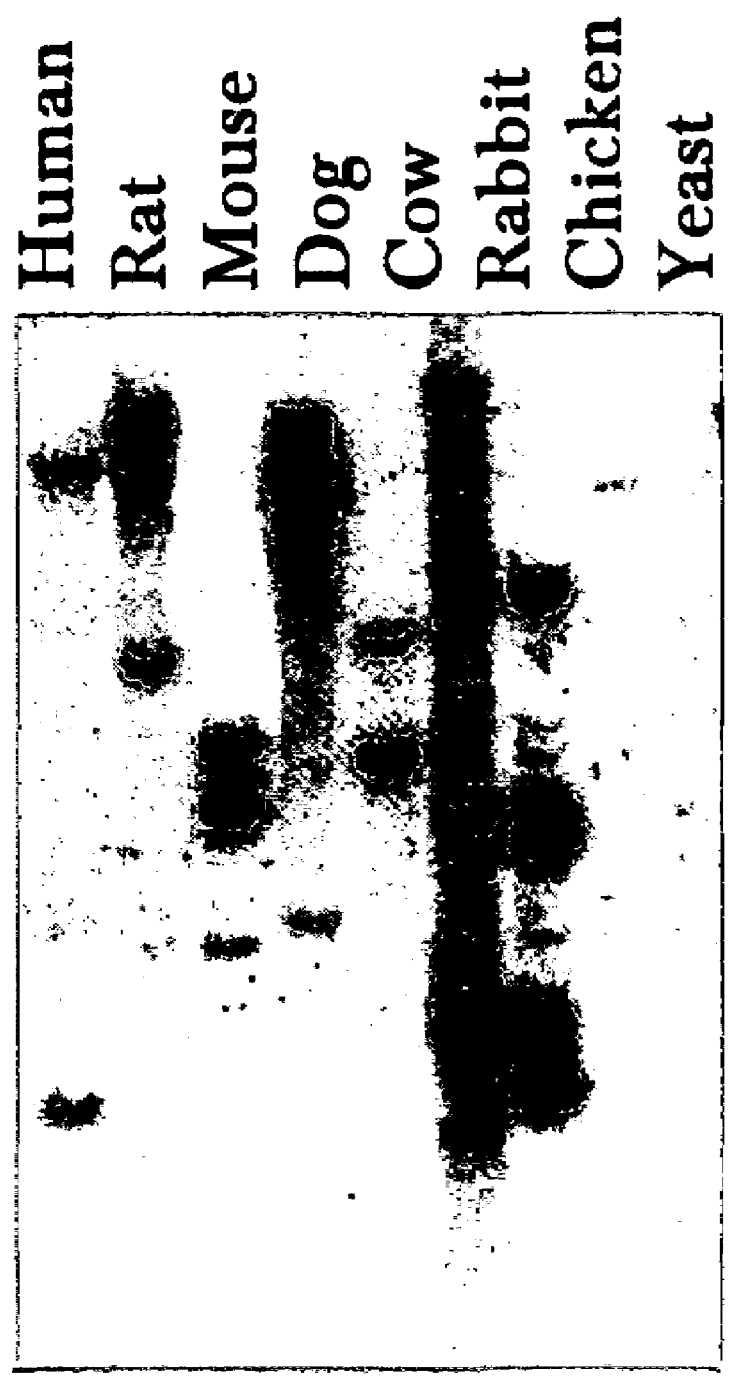
FIG. 7 shows a genomic southern blot examining BOG in different species and demonstrating that the BOG gene is present in all mammals tested.

Finally, we evaluated the impact of constitutive over-expression of BOG on the rate of spontaneous transformation of RLE cells. Cells over-expressing BOG exhibited aberrant morphology 5 to 6 passages after BOG transfection, and by passage 9, 80% of the cell population was comprised of morphologically transformed cells, as shown by smaller cell size with little cytoplasm and enlarged nucleus compared to the original early passage. This is in stark contrast to the parental RLE cells that require a minimum of 35-40 passages to begin displaying the transformed phenotype. A. C. Hugget, et al. *Cancer Res.*, 51:5929 (1991). When RLE/BOG cells were kept at a confluent stage, small colonies arose demonstrating the ability of these cells to grow in an anchorage independent manner. Further confirmation of the transformed phenotype was demonstrated by the capacity of RLE/BOG cells to grow in a soft agar and to form tumors in nude mice (FIG. 4C). Tumor phenotype was consistent with that of a highly vascular hepatoblastoma-embryonal type, similar to tumors formed by RLE cells transformed by v-raf/v-myc. S. Garfield, et al., *Mol. Carcinog*, 1:189 (1988). Southern blot analysis of RLE and B5T indicate amplification or rearrangement of the BOG gene is not the source of increased expression in these cell lines.

The cell lines used herein were first described in: Hugget. A. C. et. al. Development of resistance to the growth inhibitory effects of transforming growth factor beta 1 during the spontaneous transformation of rat liver epithelial cells. *Cancer Res.* 51, 5929 (1991), and Garfield. S. et. al. Neoplastic transformation and lineage switching of rat liver epithelial cells by retrovirus-associated oncogenes. *Mol. Carcinog.* 1, 189 (1988).

Protocols for Evaluating Constitutive Over-Expression of BOG in RLE Cell Lines. Colony Formation of Heterogeneous Population of Transfected RLE and B7 Cells Expressing BOG.

The cDNA HindIII-XbaI cDNA fragment from subtractive clone in pBluescriptM13 was subcloned into the mammalian expression vector pCDNAIneo (Invitrogen), which contains the CMV promoter and a neomycin selectable marker. The expression plasmid pCDNAI-BOG and the control vector pCDNACMV were transfected into phi 13 and B7 cells by lipofectin (Gibco BRL). After a 3 weeks selection in Ham's F-12 media containing G418 400 log activity/ml (726 µg/ml) (Sigma), colonies were harvested as mixed colonies and maintained in selective media. For the colony formation assay, $10^5$ cells for phi 13CMV (phi 13 transfected with the empty vector pCDNAIneo as a control) and phi 13 BOG (phi 13 transfected with expression plasmid pCDNAI-BOG) or $5 \times 10^4$ cells for B7CMV (B7 cells with pCDNAIneo) and B7BOG (B7 cells with pCDNAI-BOG) were plated, into 100 mm diameter dishes. The cells were allowed to attach and media containing 0.5 ng/ml TGF-β1 (R&D Systems) was added into the dishes 18 hours after plating. The medium containing 0.5 ng/ml TGF-β1 was changed every 3 days for 15 days on all plates. After 15 days of treatment the cells were fixed and the dishes were stained using crystal violet. To assess the effects of BOG on growth curves in the presence of TGF-β1, the open reading frame of BOG was subcloned into the mammalian expression vector pBKCMV (Stratagene), which contains the CMV promoter and neomycin selectable marker. Phi 13 cells were transfected with lipofectin, and grown under selection in G418 until single cell clones were visible. Several clones were picked and expanded there passages in G418 containing media. The expression level of BOG was checked by Northern blot analysis in all clones and representative clones (BOG-1 and BOG-B) were used for further experiments. To analyze for TGF-β1 growth inhibition, normal phi 13, BOG-A and BOG-B cells were plated at $5 \times 10^3$ into 96 well plates.

After 6 hours when the cells where attached, the media was chanced to Ham's F-12 media containing either 0, 100 pg/ml or 1000 pg/ml of TGF-β1. The cultures were maintained for 72 hours, after which time a cell proliferation assay was performed (Promega). The effect of TGF-β1 on growth is expressed as a percent inhibition of growth of cells grown in the presence of TGF-β1 versus cells grown in normal media for the same period of time. To examine the effect of BOG expression on the TGF-β1 receptor, phi 13, BOG-A and BOG-B cells were plated in 24-well plates and grown to 90% confluency. TGF-0 and anti-E2F-1 were both iodinated by the method of Sambrook J, Fritsch E F. Maniatis T (1989): "Molecular Cloning: A Laboratory Manual." $2^{nd}$ Ed., Cold Spring Harbor, N.Y.:Cold Spring Harbor Laboratory. Cells were analyzed in triplicate plates for each concentration of TGF-β1. Before the binding assay was performed the cells were washed once with binding buffer (Hanks' solution containing 20 mM HEPES pH 7.0) and equilibrated in the same buffer for 30 min at 4° C. Ice-cold binding buffer containing increasing concentrations of $^{125}$I-TGF-β1 (0 to 500 pM $^{125}$I-TGF-β1) was added and the preparation was incubated at 4° C. for 1 hour. Tenfold excess of unlabeled TGF-β1 was used to determine nonspecific binding and subtracted to obtain specific cpm bound. Cultures were washed 3 times with ice-cold binding buffer, and the bound and unbound (media and first two washes) $^{121}$I-TGF-β1 was measured in a LKB Rackgamma II gamma counter. Saturation curves were generated for phi 13, BOG-A and BOG-B with standard error calculated from two separate experiments.

Protocols for assessing colony formation in agar and tumor formation in nude mice. Methods for growth in soft agar and transplantation experiments were followed as described in Hugget, A. C. et. al. Development of resistance to the growth inhibitory effects of transforming growth factor beta 1 during the spontaneous transformation of rat liver epithelial cells. *Cancer Res.* 51, 5929 (1991), and Garfield, S. et. al. Neoplastic transformation and lineage switching of rat liver epithelial cells by retrovirus-associated oncogenes. *Mol. Carcinog.* 1, 189 (1988). Tumors in nude mice were derived from BOG-A cell line. Morphologically transformed BOG-A (passage 14) cells (106) cells were transplanted into nude mice. Visible tumors developed within two weeks, at which time the animal was sacrificed and tumors dissected. Tumors were fixed in 10% phosphate buffered (pH 7.4) formalin, embedded in paraffin and sections stained with hematoxylin-eosin (H&E) for histological evaluation.

Example 5

Effects of BOG Antisense Oligonucleotides on BOG Expression and TGF-β Sensitivity.

Figure 3B:
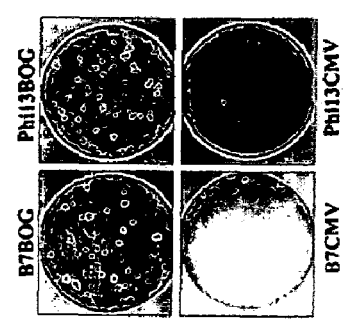
FIG. 3(B) shows growth curves in the presence of TGF-β1. RLE phi 13 cells were transfected with BOG and cell lines overexpressing BOG were selected. Two clones. BOG-A and BOG-B, representing the two extremes of BOG expression in these lines were chosen and expanded for further experiments. The effect of overexpression of BOG on the cells ability to proliferate in the presence of TGF-β1 was examined. The effect of TGF-β1 on growth is expressed as a percent inhibition of growth of cells grown in the presence of TGF-β1 versus cells grown in normal media for the same period of time. Values and standard error presented represent two separate experiments done in quadruplicate.
Figure 3C:
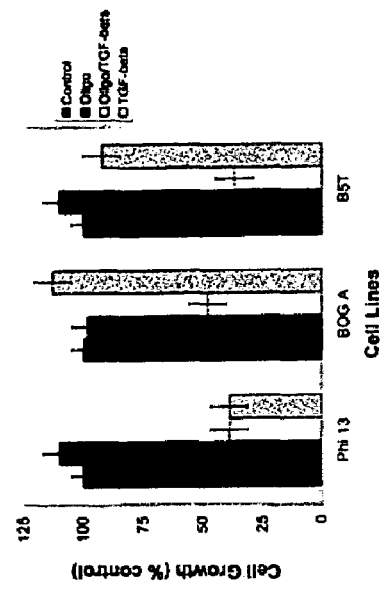
FIG. 3(C) shows the effect of BOG expression on the TGF-β1 receptor. The same cell lines used to examine growth were expanded and their ability to bind TGF-β1 was examined. Binding curves were generated using samples analyzed in triplicate for each concentration of TGF-β1. Tenfold excess of unlabeled TGF-β1 was used to determine nonspecific binding and subtracted to obtain specific cpm bound. Saturation curves were generated for phi 13. BOG-A and BOG-B with standard error calculated from two separate experiments. To further evaluate the effect of BOG on the TGF-D receptor expression. Northern blot analysis of TGF-β receptor II was performed (inset). BOG expression also was tested to confirm previous characterizations of the transgene expression (inset).
Figure 3D:
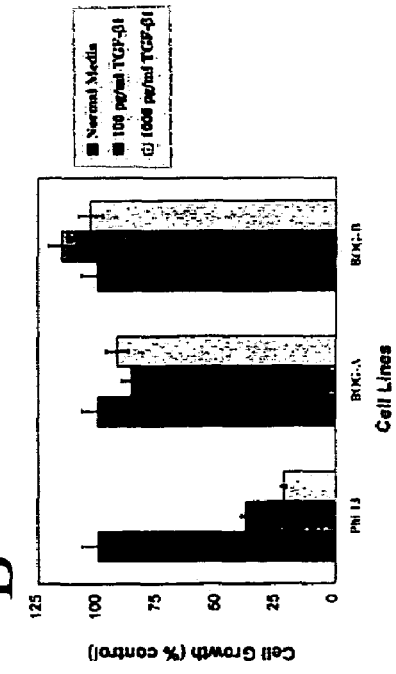
FIG. 3(D) shows the restoration of TGF-β1 sensitivity by antisense oligonucleotides to BOG. In order to decrease the amount of BOG protein, cell lines were incubated with antisense oligonucleotides to BOG. Oligonucleotide alone was not toxic to any of the cell lines as demonstrated by 100% growth as compared to the cells grown in control media.

As discussed above, the growth inhibitory effects of TGF-β1 were completely blocked by BOG over-expression (FIG. 3B). To examine if we could restore sensitivity to TGF-β1 by decreasing the amount of BOG in the cell, we incubated cells with antisense oligonucleotides to BOG. In the cell line BOG-A, that had a 3 fold overexpression of BOG, incubation with antisense oligonucleotides restored sensitivity to TGF-β1 to a level similar to that of the parental RLE cells (FIG. 3D). Moreover, sensitivity to TGF-β1 could also be restored in the B5T cell line, a transformed cell line that was less sensitive to TGF-β1, but is known to contain the full compliment of TGF-β receptors. This suggests that one of the primary causes for loss of sensitivity to TGF-β1 in these cell lines is due to the overexpression of BOG. One implication of this observation is that sensitivity to TGF-β may be restored in transformed cells which still maintain signaling through the TGF-β pathway, through methods that decrease the expression of BOG. Furthermore, since over-expression of BOG decreases sensitivity to TGF-β even in the presence of an intact TGF-β signaling pathway, BOG may be an early indicator or selection for cells destined to become transformed in vivo.

Protocols for the inhibition of BOG by anti-sense oligonucleotides. Phosphothionate-modified antisense oligonucleotides corresponding to the 5' end (AATCACTGCCT-TGGTAGGGGACACCATTAA) (SEQ ID NO:12) and the 3' end of the one reading frame (TCAGTTCATG-GAACTCTGTGTTCTGAAAGTGAC) (SEQ ID NO:13) of BOG were synthesized and purified by OPC column (Bioseme Biotechnology, Inc.). Cells were plated at 50% confluency and allowed to attach in Ham-F12 media containing 10% Fetal Bobine Serum (FBS). Once the cells were attached, they were washed once with DPBS and media containing antisense oligonucleotides (340. mu.g/ml each) and/or TGF-.beta. 1 (250 pg/ml) was added to the cells, and the cultures were allowed to grow for 48 hours. Cell growth was assayed using the Cell Titer 96 Non-radioactive Cell Proliferation Assay (CellTiter 96 Non-Radioactive Cell Proliferation Assay (cat#G4000). Promega Corporation). The concentration of TGF-β was determined by art accepted methods. In particular, the dose response of the cells to TGF-β was previously determined (Hugget, A. C. et. al.). Development of resistance to the growth inhibitory effects of transforming growth factor beta 1 during the spontaneous transformation of rat liver epithelial cells. *Cancer Res.* 51, 5929 (1991)). A dose of 0.5 ng/ml TGF-β was chosen because it was an effective dose for the cytostatic effect in all cell lines analyzed.

Example 6

Generation of a BOG-MBP Fusion Protein.

A chimeric protein (BOG-MBP) was constructed using the Protein Fusion and Purification System (New England Biolabs, Inc.). PCR protocols were utilized to generate a BOG polynucleotide having restriction endonuclease sites that allowed the complete open reading frame to be linked to the maltose binding protein (MBP). See e.g. *Current Protocols In Molecular Biology*, Volume I, Unit 17. Frederick M. Ausubul et al. eds. 1995. The pMAL-P2 vector used produced a protein in which the complete rBOG protein is fused to the carboxy-terminal of MBP (pMAL-P2-BOG). The chimeric protein was purified using an amylose resin and tested for its ability to precipitate pRb from whole cell lysates. The DNA sequence encoding an extracellular region of the BOG polypeptide.

Example 7

Preparation of Antibodies that Bind BOG.

Polyclonal antibodies to BOG was generated commercially by Genemed Synthesis, Inc. using art accepted methods. Initially, the rabbits were immunized with the fusion protein (BOG-MBP) and subsequent booster shots were done with purified 20 kDa BOG. The final serum generated recognized both BOG and MBP.

The following example illustrates preparation of monoclonal antibodies which can specifically bind BOG.

Techniques for producing the monoclonal antibodies are known in the art and are described, for instance, in Goding, supra. Immunogens that may be employed include purified BOG, fusion proteins containing BOG, and cells expressing recombinant BOG on the cell surface. Selection of the immunogen can be made by the skilled artisan without undue experimentation.

Mice, such as Balb/c, are immunized with the BOG immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research. Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect BOG antibodies.

After a suitable antibody titer has been detected, the animals "positive" for antibodies can be injected with a final intravenous injection of BOG. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids. The hybridoma cells will be screened in an ELISA for reactivity against BOG. Determination of "positive" hybridoma cells secreting the desired monoclonal antibodies against BOG is within the skill in the art.

The positive hybridoma cells can be injected intraperitoneally into syngeneic Balb/c mice to produce ascites containing the anti-BOG monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 8

Isolation and Chromosomal Localization of Human and Murine BOG DNA Sequences. DNA comprising the coding sequence of BOG was employed for use as both primers and probes to screen for homologous DNAs (such as those encoding naturally-occurring variants of BOG) in human tissue cDNA libraries, human tissue genomic libraries. Analysis of cDNA libraries from human and mouse indicate that BOG is a highly conserved gene in both these species.

The coding region of the human cDNA was isolated from a human liver cDNA library (human liver 5' stretch plus cDNA, Clonetech Laboratories, Inc.) using PCR. See Table 4. Primers were designed to the 5' (ATGGTCTCTCCTAGC) (SEQ ID NO:14) and 3' (GAGTTCCATGAAC) (SEQ ID NO: 15) portions of the open reading frame of mouse and rat BOG, and PCR was done using PCR SuperMix (Gibco, BRL Life Technologies) using company recommended conditions. The predicted 500 bp PCR fragment was cloned into the TA vector pCR2.1 (In Vitrogen.TM.), for further analysis (pCR2.1huBOG). Five clones were isolated and double strand sequenced obtained to confirm hBOG sequence.

The mouse cDNA clone was isolated from a mouse kidney cDNA library (mouse kidney 5'-stretch cDNA, Clonetech laboratories, Inc.). See Table 6. Phage were plated at $5 \times 10^5$ pfu/150 mm plate and duplicate filters were screened using a 500 bp fragment corresponding to the coding region of rBOG. Seven plaques were identified and plaque purified. The insert from these lambda clones were subcloned into the pBluescript vector (Stratagene™) for further analysis (pBSλmBOG). All clones were double strand sequenced and used to confirm overall sequence of mBOG.

Human and murine genomic clones were isolated by screening high density filters of BAC genomic libraries supplied by Genome Systems, Inc. See Tables 8 and 9.

Figure 8A:
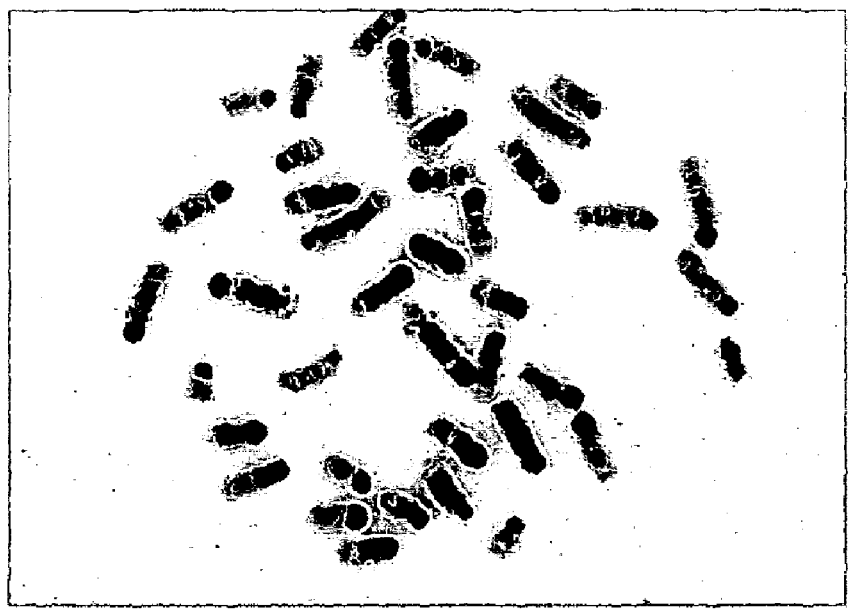
FIGS. 8(A) and 8(B) illustrate a chromosomal localization FISH analysis showing that murine BOG maps to chromosome 2.
Figure 8B:
Figure 8C:
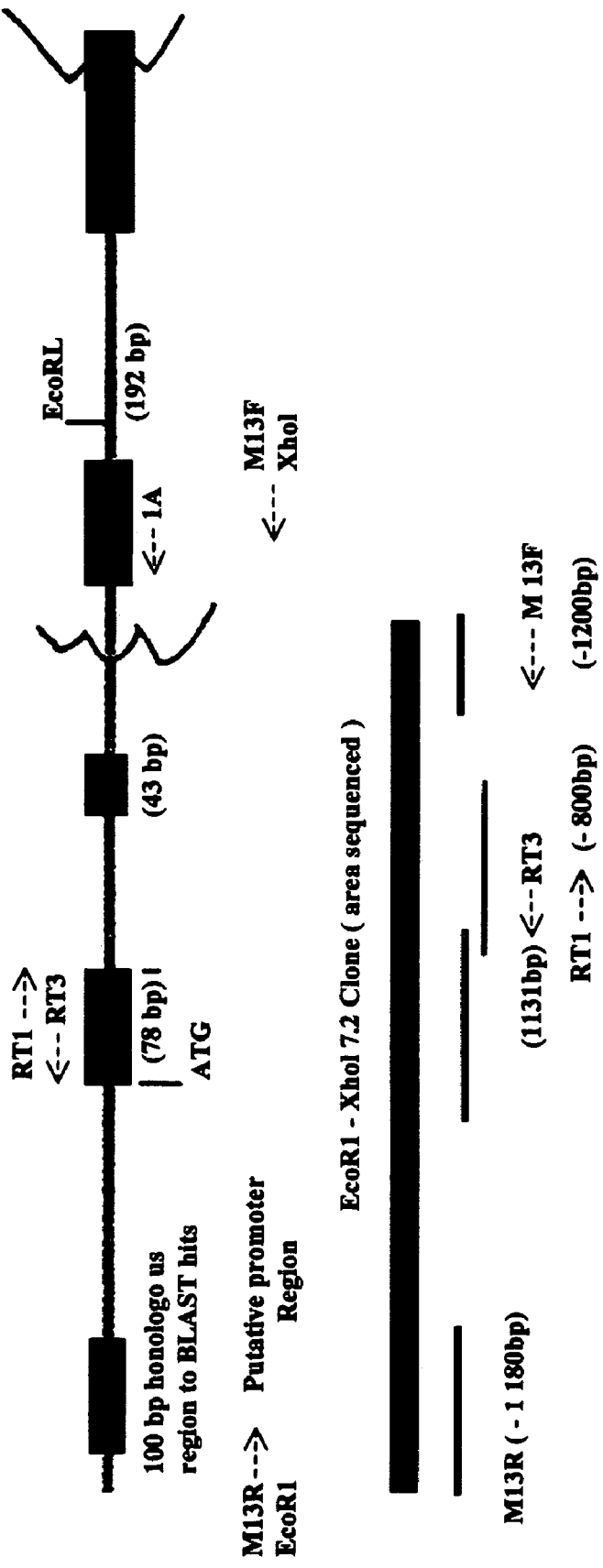
FIG. 8(C) is a representational map of the SB6 murine genomic clone.
Figure 11:
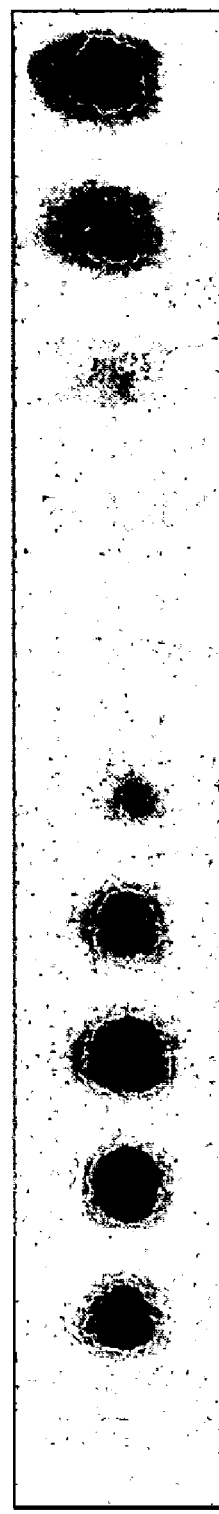
FIG. 11 shows the expression of rat BOG after partial hepotectomy. A ⅔ partial hepotectomy was performed on rats to obtain a synchronized population of primary hepatocytes. The peak expression of BOG corresponds to late G1-S.
Figure 12:
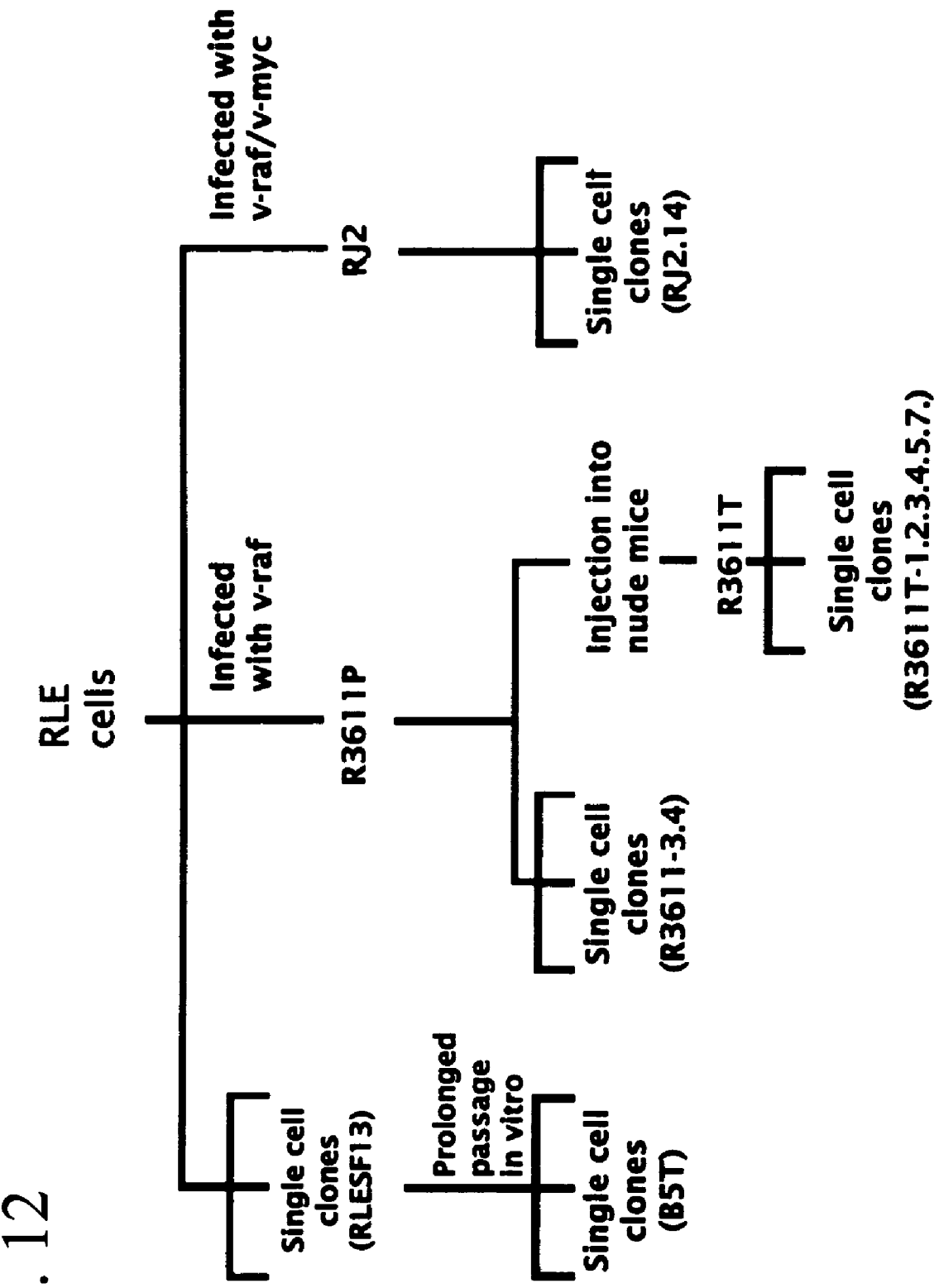
FIG. 12 shows the derivation of RLE cell lines. The RLE cell lines were derived from parental cells isolated from a 10 day old Fisher 344 rat and untransformed and transformed cell lines were derived from this original population.

Chromosomal localization was done by FISH analysis (Stokke, T., Collins, C., Kuo, W. Kowbel, D., Shadrvan, F., Tanner, M., Kallionienmi, A., Kallioniemi, O., Pinkel, D., Deaven, L., and Gray, J; A physical map of chromosome 20 established using fluorescent in situ hybridization (FISH) and digital image analysis. Genomics 26: 134-137 (1995). BOG maps to murine chromosome 2. In humans. BOG maps to the syntenic region of chromosome 20. See FIGS. 8A and 8B.

Example 9

Evaluation of BOG Expression During Cell Cycling. All cell lines as mentioned above were routinely maintained in Ham's F-12 medium supplemented with 10% defined fetal bovine serum (Biofluids, Rockville, Md.) and 50 ug/ml gentamicin (GIBCO, Grand Island, N.Y.) at 37° C. in a humidified atmosphere of 5% CO2 and 95% air. Cells were grown in 162 cm² plastic flasks and passaged at a ratio 1:8 every 4 days using 0.1% trypsin solution in versene (Biofluids) for cell detachment.

Cells were plated in 162 cm² plastic flasks at $2 \times 10^6$ cells/flask for RLE-13 cells and at $3 \times 10^6$/flask for B5T cells. Synchronization was done following 3 types of protocols. For synchronization by Lovastatin treatment, medium was removed 24-36 hours after the initial plating and replaced with fresh medium containing Lovastatin at 10 uM for RLE-13 cells and 30 uM for B5T cells. To release cells from this block, after 24 hour incubation (time 0 hour) the medium was removed and replaced with fresh medium containing mevalonic acid at a concentration 100 times the Lovastatin concentration used. For experiments measuring effects of TGF-β1 on BOG expression during cell cycle TGF-β1 (250 pg/ml) was added in the fresh medium. Cells were harvested at the indicated times using 0.1% trypsin solution in versene for flow cytometer analysis For synchronization by serum deprivation, cells were incubated with Ham's F12 medium containing 0.2% defined fetal bovine serum for 72 hours. At time 0 hours, the low serum medium was removed and the cells were stimulated by addition of complete medium containing 10% serum. For synchronization by mimosine; aphidicolin and nocadazole, medium was removed and replaced with fresh medium containing 200 uM mimosine (Aldrich), 5 ug/ml aphidicolin (Sigma) or 400 ng/ml nocadazole (Janssen). Cells were harvested by trypsinization and centrifugation. For RNA isolation, cells were lysed in 4M guanidine thiocyanate solution. For flow cytometer analysis, cells were fixed by dehydration in 70% ethanol and stored at 4° C. prior to analysis. Cells were then washed once with ice-cold PBS, treated with 500 units of RNase A (Boehringer Mannheim) per ml for 15' at 37° C. Cellular DNA was stained with 50 ug of propidium iodide per ml for a minimum of 30 minutes prior to flow cytometer analysis. Cell cycle determination was performed using a Becton-Dickinson Fluorescence-Activated Cell Analyzer and data were collected on the FL2 channel using a 640 nm band pass filter. Results represent a minimum of 10,000 cells assayed for each determination. Results of these experiments demonstrate that transcription of BOG is cell-cycle regulated, having high expression in Go, decreasing in early G1, and increasing and peaking in expression late G1/S. See FIGS. 10A and 10B.

Protocols to establish the nuclear localization of BOG polypeptides were performed following art accepted immunohistochemical methods using anti-BOG antibodies. See FIGS. 9A and 9B.

Table 1 shows the cDNA (SEQ ID NO: 1) and amino acid (SEQ ID NO: 2) sequences of rat BOG as determined by double strand sequence analysis of a 1.9 kb clone. The potential Rb binding domain is indicated by the underline and the two putative casein kinase II phosphorylation sites by boldface type.

```
GTCTCACGTC TGCATTA ATG GTG TCC CCT ACC AAG GCA GTG ATT GTT CCT            50
                    MET VAL SER PRO THR LYS ALA VAL ILE VAL PRO
                     1               5                  10

GGG AAC GGA GGC GGG GAT GTG GCC ACC CAC GGC TGG TAC GGC TGG GTG           98
GLY ASN GLY GLY GLY ASP VAL ALA THR HIS GLY TRP TYR GLY TRP VAL
                15                  20                  25

AGA AAG GGG CTG GAG CAG ATT CCT GGT TTC CAG TGT TTG GCT AAA AAC          146
ARG LYS GLY LEU GLU GLN ILE PRO GLY PHE GLN CYS LEU ALA LYS ASN
            30                  35                  40

ATG CCT GAC CCA ATT ACC GCT CGA GAG AGC ATC TGG CTG CCC TTC ATG          194
MET PRO ASP PRO ILE THR ALA ARG GLU SER ILE TRP LEU PRO PHE MET
        45                  50                  55

GAG ACA GAA CTG CAC TGT GAT GAG AAG ACC ATC ATC ATA GGC CAC AGT          242
GLU THR GLU LEU HIS CYS ASP GLU LYS THR ILE ILE ILE GLY HIS SER
 60             65                  70                      75

TCC GGG GCC ATC GCA GCC ATG AGG TAT GCA GAG ACA CAT CAG GTA TAC          290
SER GLY ALA ILE ALA ALA MET ARG TYR ALA GLU THR HIS GLN VAL TYR
                80                  85                  90

GCT CTC ATA TTG GTG TCT GCA TAC ACA TCA GAC TTG GGA GAT GAA AAT          338
ALA LEU ILE LEU VAL SER ALA TYR THR SER ASP LEU GLY ASP GLU ASN
                95                 100                 105

GAG CGT GCA AGT GGG TAC TTC AGC CGC CCC TGG CAG TGG GAG AAG ATC          386
GLU ARG ALA SER GLY TYR PHE SER ARG PRO TRP GLN TRP GLU LYS ILE
       110                  115                 120

AAG GCC AAC TGC CCT CAC ATT ATA CAG TTT GGC TCT ACT GAT GAC CCC          434
LYS ALA ASN CYS PRO HIS ILE ILE GLN PHE GLY SER THR ASP ASP PRO
       125                  130                 135

TTC CTT CCA TGG AAG GAA CAA CAA GAA GTG GCA GAT AGC TGG ACG CCA          482
PHE LEU PRO TRP LYS GLU GLN GLN GLU VAL ALA ASP SER TRP THR PRO
140                 145                 150                 155

AAC TGT ACA AAT TCA CTG ACC GTG GTC ACT TTC AGA ACA CAG AGT TCC          530
ASN CYS THR ASN SER LEU THR VAL VAL THR PHE ARG THR GLN SER SER
                160                 165                 170

ATG AAC TGATTAGAGT GGTGAAGTCT ATGCTGACTC CTGCTCTGTA ACACGCCAGG           586
MET ASN

ATGGGGTAGA AGAGTAACAG CCGCTACCCT CACACAGCTT AGACATGGAC GTCCGTCCAG        646

TTAGACTACA GAAGTGTCTG AGCAACAAAC CCATTTGAAC ACTCACACTG AGTTAGTAGC        706

ACTTCCAGTT CCCACAGAGC TTAAATCTCC CCAAAAGCTA CTAGCTACAG CAGTATGTTT        766

CCTGTTTGAT AAGAGACAGG TTTTTTATTT TTAAGCTATC CTGTTGATGC AAAGAGAGTT        826

AAGTCAGAAG AATCCAGAAC TTGACATAGA CCTGGTTGTG TGTCCCTGTA ATCATTTCAG        886

AAAGCAGGGT CAGGAGGGAA GGCTATCTTG ACCCTGTCTC AGAAAGAGTG AGCAAGAAGA        946

TGACCCAGGT CTCCTGAGGC TCATTCCAAA TTATAACTCA CTATGTTTAG CAAGATGTGT       1006

TCCACTTCTG AGACCCCAGT ACTTGGAAAA CTGAGGAAGG TTCATCTTGA GTTTGAGACC       1066

TTGTCTAGGC TAAGTAAACC CTGTCTCAAA ACAACAACAA AAACAGGTTT TCATTCAACT       1126

TATATGACTG ACACTTTCCA TTTGTAATAA AAAATTTTCT CTTACTGGGG AAATGAAAAC       1186
```

Table 1 shows the cDNA (SEQ ID NO: 1) and amino acid (SEQ ID NO: 2) sequences of rat BOG as determined by double strand sequence analysis of a 1.9 kb clone. The potential Rb binding domain is indicated by the underline and the two putative casein kinase II phosphorylation sites by boldface type.

```
ACGATTCAAG GTCCAGAATG TTGTCTTAGA ACTCAAAACT CTGGTTGCTC TTTAAAACTG   1246

GCTCAAGAGA ATAAACTCAA ACTTGGGTGT TCATCATTGA AATTCCTGAC CCCACCACGT   1306

CCCCAACCGT CCAGACTCTA CAGTGAGAGT GACACATATG ATGCTAGTAG ACTGCAGGCA   1366

GTATCTGTTA TACACTGTAT AGACTGCAGA TTCGATCATG GGAGTGCTGC AATATAGAAA   1426

TGTGACCTAT GTCTTTTTTA CTAGAGAATA TAGTGTGTAT ATAATTCCTA CATGAATTAT   1486

GGTAACTGGG AACAGCATTG TAATTAAAAG ATTTGCAAAT GCTACTACAA GACAAAGACC   1546

AGGTCATCCC TTTGTGAACT TGGTCGTAAA CATTTTTAGA ATCTCTATGA AGTCCAAGAA   1606

AAACAAGATA ACTAAAATGA CATAATACTA AAGGGTGGAA AACAAGGAGC AATCGTATTT   1666

TGTTATTAAG TTTTTAAGTA TCTTCAAAAG AACTTTTCCA GGGCTAGGGA GAAGGCTGAC   1726

AGTCAAGAGG CTACTGAGTT TTTTTCCAGA GTTCTGAGTT CAATTCCCAG CAACTACATG   1786

GTAGTCACAA CCATCTGTAA TGGACCCGAT GCCCTCTTCT GGTGTGTCTG AAGACAGCTA   1846

CAGTGTACTC ACATACATAA AATAAGTAAA TCTTAAAAAA AAAAAAAAA A             1897
```

Table 2 shows amino acid sequence homology of the BOG pRb binding domain (SEQ ID NO: 2) and casein kinase II consensus sequence to the Rb binding proteins Human Papilloma Virus E7 (SEQ ID NO: 3), Simian Virus 40 large T antigen (SEQ ID NO: 4), Adenovirus E1A (SEQ ID NO: 5) and RBP-1 (SEQ ID NO: 6) is illustrated by alignment of the Rb binding domain (LXCXE) (bold) and casein kinase II phosphorylation sites (underlined).

| | | |
|---|---|---|
| BOG | L P F M E T E - L H C D E K T I | (-44aa) - S T D D |
| HPV16E7 | D L Q P E T T D L Y C Y E Q - L N D | S S E E E |
| SV40 LT | N A F N E - E N L F C S E E - M P - | S S D D E |
| AD5 E1A | N L V P E V I D L T C H E A G F P P - - | S D D E |
| RBP-1 | L I G P E T - - L V C H E V D L | (-8aa) T S E I D |

Table 3 shows the total amino acid sequence homology of rBOG (SEQ ID NO: 2) and E7 (SEQ ID NO: 3) showing that rBOG is 38% homologous to E7.

```
rBOG    MVSPTKAVIVPGNGGGDVATHGWYGWVRKGLEQIPGFQCLAKNMPDPITA   50
HPV-E7  MH------------GDTPT------------------LHEYMLD---- rBOG    RESIWLPFMETELHCDEKTIIIGHSSGAIAAMRYAETHQVYALILVSAYT  100
HPV-E7  -----LQPETTDLYCYEQ---LNDSSEE--------------------- rBOG    SDLGDENERASGYFSRPWQWEKIKANCPHIIQFGSTDDPFLPWKEQQEVA  150
HPV-E7  ---EDEIDGPAG------QAEPDRAHY-NIVTFCCKCDSTLRLCVQSTHV rBOG    DSWTPNCTNSLTVVTFRTQSSMN   173    Identity:    29.6%
HPV-E7  DIRTLEDLLMGTLGIVCPICSQKP   98    Similarity:   7.1%
```

| Table 4 shows the cDNA coding sequence of human BOG. (SEQ ID NO: 7) |     |
| --- | --- |
| ATGGTGTCCC CCAGCAAGGC AGTGATTGTT CCCGGGAAGA TAGGTGGGGA TGAGACCACC | 60 |
| CACGGCTGGT ATGGCTGGGT GAAAAAGGAG CTGGAGAAGA TACCTGGTTT CCAGTGTTTG | 120 |
| GCTAAAAACA TGCCCGACCC AATTACCGCG CGAGAGAGCA TCTGGCTGCC CTTCATGGAG | 180 |
| ACAGAACTGC ACTGTGATGA AGAGACTATC ATCATTGGCC ACAGTTCCGG GGCCATCGCG | 240 |
| GCCATGAGGT ATGCAGAAAC ACATCGAGTA TATGCTCTCA TATTGGTGTC TGCATACACA | 300 |
| TCAGAGTTTG GAGATGAAAA TGAGCGTGCA AGTGGGTACT TCAGCCGCCC CTGGCAGTGG | 360 |
| GAGAAGATCA AGGCCAACTG CCCTCACATT GTACAGTTTG GCTCTACTGA TGACCCCTTC | 420 |
| CTTCCCTGGA AGGAACAACA AGAAGTGGCA GATAGCTGGA CGCCAAATTG TACAAATTCA | 480 |
| CTGACCGTGG TCACTTTCAG AACACAGAGT TCCATGAACT GA | 522 |

| Table 5 shows the amino acid sequence of human BOG protein. (SEQ ID NO: 8) |     |
| --- | --- |
| MVSPSKAVIVPGKIGGDETTHGWYGWVKKELEKIPGFQCLAKNMP DPITA | 050 |
| RESIWLPFMETELHCDEKTIIIGHSSGAIAAMRYAETHRVYALIL VSAYT | 100 |
| SEFGDENERASGYFSRPWQWEKIKANCPHIVQFGSTDDPFLPWKE QQEVA | 150 |
| DSWTPNCTNSLTVVTFRTQSSMN | 173 |

| Table 6 shows the cDNA coding sequence of murine BOG. (SEQ ID NO: 9) |     |
| --- | --- |
| ATGGCGTCCC CCAACAAGGC AGTGATTGTT CCTGGGAACG GAGGCGGGGA TGTGGCCACC | 060 |
| CACGGCTGGT ATGGCTGGGT GAAAAAGGGG CTGGAGCAGA TTCCTGGTTT CCAGTGTTTG | 120 |
| GCTAAAAACA TGCCTGACCC AATTACCGCG CGAGAGAGCA TCTGGCTGCC CTTCATGGAG | 180 |
| ACAGAGCTGC ACTGTGACGA GAAGACCATC ATCATAGGCC ACAGTTCCGG GGCCATCGCA | 240 |
| GCCATGAGGT ATGCAGAGAC ACATCAGGTA TACGCTCTCG TATTGGTGTC TGCATACACA | 300 |
| TCAGACTTGG GAGATGAAAA TGAGCGTGCA AGTGGGTACT TCAGCCGCCC CTGGCAGTGG | 360 |
| GAGAAGATCA AGGCCAACTG CCCTCACATT ATACAGTTTG GCTCTACTGA TGACCCCTTC | 420 |
| CTTCCCTGGA AGGAACAACA AGAAGTGGCA GATAGCTGGA CGCCAAATTG TACAAATTCA | 480 |
| CTGACCGTGG TCACTTTCAG AACACAGAGT TCCATGAACT GA | 522 |

Table 7 shows the amino acid sequence of murine BOG protein. (SEQ ID NO: 10)

| | |
|---|---|
| MASPNKAVIVPGNGGGDVATHGWYGWVKKGLEQIPGFQCLAKNMP DPITA | 050 |
| RESIWLPFMETELHCDEKTIIIGHSSGAIAAMRYAETHQVYALVL VSAYT | 100 |
| SDLGDENERASGYFSRPWQWEKIKANCPHIIQFGSTDDPFLPWKE QQEVAD | 150 |
| SWTPNCTNSLTVVTFRTQSSMN | 173 |

Table 8 shows a comparison of the amino acid sequence of the murine (SEQ ID NO: 10), human (SEQ ID NO: 8) and rat BOG (SEQ ID NO: 2) proteins.

```
Murine  MASPNKAVIVPGNGGGDVATHGWYGWVKKGLEQIPGFQCLAKNMPDPITA   050
Rat     MVSPTKAVIVPGNGGGDVATHGWYGWVRKGLEQIPGFQCLAKNMPDPITA
Human   MVSPSKAVIVPGKIGGDETTHGWYGWVKKELEKIPGFQCLAKNMPDPITA Murine  RESIWLPEMETELHCDEKTIIIGHSSGAIAAMRYAETHQVYALVLVSAYT   100
Rat     RESIWLPEMETELHCDEKTIIIGHSSGAIAAMRYAETHQVYALILVSAYT
Human   RESIWLPFMETELHCDEKTIIIGHSSGAIAAMRYAETHRVYALILVSAYT Murine  SDLGDENERASGYFSRPWQWEKIKANCPHIIQFGSTDDPFLPWKEQQEVA   150
Rat     SDLGDENERASGYFSRPWQWEKIKANCPHIIQFGSTDDPFLPWKEQQEVA
Human   SEFGDENERASGYFSRPWQWEKIKANCPHIVQFGSTDDPFLPWKEQQEVA Murine  DSWTPNCTNSLTVVTFRTQSSMN                              173
Rat     DSWTPNCTNSLTVVTFRTQSSMN
Human   DSWTPNCTNSLTVVTFRTQSSMN
```

What is claimed is:

1. An isolated polypeptide comprising
    BOG polypeptide comprising
       (i) at least 90% amino acid sequence identity with SEQ ID NO: 8;
       (ii) a retinoblastoma gene product (pRB) binding motif; and
       (iii) at least one casein kinase II phosphorylation motif; wherein the polypeptide binds pRB and displaces the transcriptional factor E2F-1 bound to pRB.

2. The BOG polypeptide claim 1, wherein said casein kinase II phosphorylation motif is located downstream of the pRb binding motif.

3. The BOG polypeptide of claim 2, further comprising a second casein kinase II phosphorylation motif, said second casein kinase II phosphorylation motif being located upstream of the pRb binding motif.

4. The BOG polypeptide of claim 1 joined to a detectable label.

5. The BOG polypeptide of claim 4, wherein the detectable label includes a radioactive isotope, an enzyme, a chromophore or a mixture thereof.

6. A chimeric molecule comprising the BOG polypeptide of claim 1 fused to a heterologous amino acid sequence.

7. An isolated polypeptide comprising:
    i) at least 95% amino acid sequence identity with SEQ ID NO:8
    ii) a retinoblastoma gene product (pRB) binding motif; and
    iii) at least one casein kinase II phosphorylation motif; wherein the polypeptide binds pRB and displaces the transcriptional factor E2F-1 bound to pRB.

8. The polypeptide of claim 7 comprising the amino acid sequence of SEQ ID NO:8.

9. The polypeptide of claim 7, wherein said casein kinase II phosphorylation motif is located downstream of the pRB binding motif.

10. The polypeptide of claim 9 further comprising a second casein II phosphorylation motif, said second casein kinase II phosphorylation motif being located upstream of the pRB binding motif.

11. The polypeptide of claim 7 joined to a detectable label.

12. The polypeptide of claim 11, wherein the detectable label comprises a radioactive isotope, an enzyme, a chromophore or a mixture thereof.

13. The polypeptide of claim 7 further comprising a heterologous amino acid sequence.

14. The polypeptide of claim 13, wherein the heterologous amino acid is a tag polypeptide.

15. The polypeptide of claim 13, wherein the heterologous amino acid sequence is that of an immunoglobulin constant region.

16. The polypeptide of claim 13, wherein the heterologous amino acid sequence is maltose binding protein.

17. An isolated polypeptide comprising a polypeptide having 95% sequence identity to the amino acid sequence of SEQ ID NO:8, wherein the isolated polypeptide binds the retinoblastoma gene product (pRB) and displaces the transcriptional factor E2F-1 bound to pRB.

18. The isolated polypeptide of claim 17, comprising the amino acid sequence of SEQ ID NO:8.

19. The isolated polypeptide of claim 1, comprising a polypeptide having 95% sequence identity to the amino acid sequence of SEQ ID NO:8.

20. The isolated polypeptide of claim 19, comprising the amino acid sequence of SEQ ID NO:8.

* * * * *

SEQUENCE LISTING

<160> NUMBER OF SEQ ID NOS: 15

<210> SEQ ID NO 1
<211> LENGTH: 1897
<212> TYPE: DNA
<213> ORGANISM: Rattus norvegicus
<220> FEATURE:
<221> NAME/KEY: CDS
<222> LOCATION: (18)..(536)
<223> OTHER INFORMATION:

<400> SEQUENCE: 1

```
gtctcacgtc tgcatta atg gtg tcc cct acc aag gca gtg att gtt cct        50
                   Met Val Ser Pro Thr Lys Ala Val Ile Val Pro
                    1               5                   10 ggg aac gga ggc ggg gat gtg gcc acc cac ggc tgg tac ggc tgg gtg       98
Gly Asn Gly Gly Gly Asp Val Ala Thr His Gly Trp Tyr Gly Trp Val
            15                  20                  25 aga aag ggg ctg gag cag att cct ggt ttc cag tgt ttg gct aaa aac      146
Arg Lys Gly Leu Glu Gln Ile Pro Gly Phe Gln Cys Leu Ala Lys Asn
        30                  35                  40 atg cct gac cca att acc gct cga gag agc atc tgg ctg ccc ttc atg      194
Met Pro Asp Pro Ile Thr Ala Arg Glu Ser Ile Trp Leu Pro Phe Met
    45                  50                  55 gag aca gaa ctg cac tgt gat gag aag acc atc atc ata ggc cac agt      242
Glu Thr Glu Leu His Cys Asp Glu Lys Thr Ile Ile Ile Gly His Ser
```

```
              60                 65                  70                  75
tcc ggg gcc atc gca gcc atg agg tat gca gag aca cat cag gta tac       290
Ser Gly Ala Ile Ala Ala Met Arg Tyr Ala Glu Thr His Gln Val Tyr
                     80                  85                  90 gct ctc ata ttg gtg tct gca tac aca tca gac ttg gga gat gaa aat       338
Ala Leu Ile Leu Val Ser Ala Tyr Thr Ser Asp Leu Gly Asp Glu Asn
             95                 100                 105 gag cgt gca agt ggg tac ttc agc cgc ccc tgg cag tgg gag aag atc       386
Glu Arg Ala Ser Gly Tyr Phe Ser Arg Pro Trp Gln Trp Glu Lys Ile
            110                 115                 120 aag gcc aac tgc cct cac att ata cag ttt ggc tct act gat gac ccc       434
Lys Ala Asn Cys Pro His Ile Ile Gln Phe Gly Ser Thr Asp Asp Pro
        125                 130                 135 ttc ctt cca tgg aag gaa caa caa gaa gtg gca gat agc tgg acg cca       482
Phe Leu Pro Trp Lys Glu Gln Gln Glu Val Ala Asp Ser Trp Thr Pro
140                 145                 150                 155 aac tgt aca aat tca ctg acc gtg gtc act ttc aga aca cag agt tcc       530
Asn Cys Thr Asn Ser Leu Thr Val Val Thr Phe Arg Thr Gln Ser Ser
                160                 165                 170 atg aac tgattagagt ggtgaagtct atgctgactc ctgctctgta acacgccagg        586
Met Asn atggggtaga agagtaacag ccgctaccct cacacagctt agacatggac gtccgtccag     646
ttagactaca gaagtgtctg agcaacaaac ccatttgaac actcacactg agttagtagc     706
acttccagtt cccacagagc ttaaatctcc ccaaaagcta ctagctacag cagtatgttt     766
cctgtttgat aagagacagg ttttttattt ttaagctatc ctgttgatgc aaagagagtt     826
aagtcagaag aatccagaac ttgacataga cctggttgtg tgtccctgta atcatttcag     886
aaagcagggt caggagggaa ggctatcttg accctgtctc agaaagagtg agcaagaaga     946
tgacccaggt ctcctgaggc tcattccaaa ttataactca ctatgtttag caagatgtgt    1006
tccacttctg agaccccagt acttggaaaa ctgaggaagg ttcatcttga gtttgagacc    1066
ttgtctaggc taagtaaacc ctgtctcaaa acaacaacaa aaacaggttt tcattcaact    1126
tatatgactg acactttcca tttgtaataa aaaattttct cttactgggg aaatgaaaac    1186
acgattcaag gtccagaatg ttgtcttaga actcaaaact ctggttgctc tttaaaactg    1246
gctcaagaga ataaactcaa acttgggtgt tcatcattga aattcctgac cccaccacgt    1306
ccccaaccgt ccagactcta cagtgagagt gacacatatg atgctagtag actgcaggca    1366
gtatctgtta tacactgtat agactgcaga ttcgatcatg ggagtgctgc aatatagaaa    1426
tgtgacctat gtcttttttta ctagagaata tagtgtgtat ataattccta catgaattat    1486
ggtaactggg aacagcattg taattaaaag atttgcaaat gctactacaa gacaaagacc    1546
aggtcatccc tttgtgaact tggtcgtaaa catttttaga atctctatga agtccaagaa    1606
aaacaagata actaaaatga cataatacta aagggtggaa acaaggagc aatcgtatt     1666 tgttattaag tttttaagta tcttcaaaag aacttttcca gggctaggga gaaggctgac    1726
agtcaagagg ctactgagtt tttttccaga gttctgagtt caattcccag caactacatg    1786
gtagtcacaa ccatctgtaa tggacccgat gccctcttct ggtgtgtctg aagacagcta    1846
cagtgtactc acatacataa aataagtaaa tcttaaaaaa aaaaaaaaa a              1897
```

<210> SEQ ID NO 2
<211> LENGTH: 173
<212> TYPE: PRT
<213> ORGANISM: Rattus norvegicus

<400> SEQUENCE: 2

```
Met Val Ser Pro Thr Lys Ala Val Ile Val Pro Gly Asn Gly Gly Gly
1               5                   10                  15

Asp Val Ala Thr His Gly Trp Tyr Gly Trp Val Arg Lys Gly Leu Glu
            20                  25                  30

Gln Ile Pro Gly Phe Gln Cys Leu Ala Lys Asn Met Pro Asp Pro Ile
        35                  40                  45

Thr Ala Arg Glu Ser Ile Trp Leu Pro Phe Met Glu Thr Glu Leu His
    50                  55                  60

Cys Asp Glu Lys Thr Ile Ile Gly His Ser Ser Gly Ala Ile Ala
65                  70                  75                  80

Ala Met Arg Tyr Ala Glu Thr His Gln Val Tyr Ala Leu Ile Leu Val
                85                  90                  95

Ser Ala Tyr Thr Ser Asp Leu Gly Asp Glu Asn Glu Arg Ala Ser Gly
            100                 105                 110

Tyr Phe Ser Arg Pro Trp Gln Trp Glu Lys Ile Lys Ala Asn Cys Pro
        115                 120                 125

His Ile Ile Gln Phe Gly Ser Thr Asp Pro Phe Leu Pro Trp Lys
    130                 135                 140

Glu Gln Gln Glu Val Ala Asp Ser Trp Thr Pro Asn Cys Thr Asn Ser
145                 150                 155                 160

Leu Thr Val Val Thr Phe Arg Thr Gln Ser Ser Met Asn
                165                 170
```

<210> SEQ ID NO 3
<211> LENGTH: 98
<212> TYPE: PRT
<213> ORGANISM: Human papillomavirus

<400> SEQUENCE: 3

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro
```

<210> SEQ ID NO 4
<211> LENGTH: 20
<212> TYPE: PRT
<213> ORGANISM: Simian virus

<400> SEQUENCE: 4

```
Asn Ala Phe Asn Glu Glu Asn Leu Phe Cys Ser Glu Glu Met Pro Ser
1               5                   10                  15

Ser Asp Asp Glu
            20
```

<210> SEQ ID NO 5

```
<211> LENGTH: 22
<212> TYPE: PRT
<213> ORGANISM: Adenovirus

<400> SEQUENCE: 5

Asn Leu Val Pro Glu Val Ile Asp Leu Thr Cys His Glu Ala Gly Phe
1               5                   10                  15

Pro Pro Ser Asp Asp Glu
            20

<210> SEQ ID NO 6
<211> LENGTH: 19
<212> TYPE: PRT
<213> ORGANISM: Homo sapiens

<400> SEQUENCE: 6

Leu Ile Gly Pro Glu Thr Leu Val Cys His Glu Val Asp Leu Thr Ser
1               5                   10                  15

Glu Ile Asp

<210> SEQ ID NO 7
<211> LENGTH: 522
<212> TYPE: DNA
<213> ORGANISM: Homo sapiens

<400> SEQUENCE: 7
atggtgtccc ccagcaaggc agtgattgtt cccgggaaga taggtgggga tgagaccacc      60
cacggctggt atggctgggt gaaaaaggag ctggagaaga tacctggttt ccagtgtttg     120
gctaaaaaca tgcccgaccc aattaccgcg cgagagagca tctggctgcc cttcatggag     180
acagaactgc actgtgatga agagactatc atcattggcc acagttccgg ggccatcgcg     240
gccatgaggt atgcagaaac acatcgagta tatgctctca tattggtgtc tgcatacaca     300
tcagagtttg gagatgaaaa tgagcgtgca agtgggtact tcagccgccc ctggcagtgg     360
gagaagatca aggccaactg ccctcacatt gtacagtttg gctctactga tgacccttc     420 cttccctgga aggaacaaca agaagtggca gatagctgga cgccaaattg tacaaattca     480
ctgaccgtgg tcactttcag aacacagagt ccatgaactg a                        522

<210> SEQ ID NO 8
<211> LENGTH: 173
<212> TYPE: PRT
<213> ORGANISM: Homo sapiens

<400> SEQUENCE: 8

Met Val Ser Pro Ser Lys Ala Val Ile Val Pro Gly Lys Ile Gly Gly
1               5                   10                  15

Asp Glu Thr Thr His Gly Trp Tyr Gly Trp Val Lys Lys Glu Leu Glu
            20                  25                  30

Lys Ile Pro Gly Phe Gln Cys Leu Ala Lys Asn Met Pro Asp Pro Ile
        35                  40                  45

Thr Ala Arg Glu Ser Ile Trp Leu Pro Phe Met Glu Thr Glu Leu His
    50                  55                  60

Cys Asp Glu Lys Thr Ile Ile Ile Gly His Ser Ser Gly Ala Ile Ala
65                  70                  75                  80

Ala Met Arg Tyr Ala Glu Thr His Arg Val Tyr Ala Leu Ile Leu Val
                85                  90                  95

Ser Ala Tyr Thr Ser Glu Phe Gly Asp Glu Asn Glu Arg Ala Ser Gly
            100                 105                 110
```

```
Tyr Phe Ser Arg Pro Trp Gln Trp Glu Lys Ile Lys Ala Asn Cys Pro
            115                 120                 125

His Ile Val Gln Phe Gly Ser Thr Asp Asp Pro Phe Leu Pro Trp Lys
        130                 135                 140

Glu Gln Gln Glu Val Ala Asp Ser Trp Thr Pro Asn Cys Thr Asn Ser
145                 150                 155                 160

Leu Thr Val Val Thr Phe Arg Thr Gln Ser Ser Met Asn
                165                 170
```

```
<210> SEQ ID NO 9
<211> LENGTH: 522
<212> TYPE: DNA
<213> ORGANISM: Mus musculus
<220> FEATURE:
<221> NAME/KEY: CDS
<222> LOCATION: (1)..(522)
<223> OTHER INFORMATION:

<400> SEQUENCE: 9
```

```
atg gcg tcc ccc aac aag gca gtg att gtt cct ggg aac gga ggc ggg        48
Met Ala Ser Pro Asn Lys Ala Val Ile Val Pro Gly Asn Gly Gly Gly
1               5                   10                  15 gat gtg gcc acc cac ggc tgg tat ggc tgg gtg aaa aag ggg ctg gag        96
Asp Val Ala Thr His Gly Trp Tyr Gly Trp Val Lys Lys Gly Leu Glu
            20                  25                  30 cag att cct ggt ttc cag tgt ttg gct aaa aac atg cct gac cca att       144
Gln Ile Pro Gly Phe Gln Cys Leu Ala Lys Asn Met Pro Asp Pro Ile
        35                  40                  45 acc gcg cga gag agc atc tgg ctg ccc ttc atg gag aca gag ctg cac       192
Thr Ala Arg Glu Ser Ile Trp Leu Pro Phe Met Glu Thr Glu Leu His
    50                  55                  60 tgt gac gag aag acc atc atc ata ggc cac agt tcc ggg gcc atc gca       240
Cys Asp Glu Lys Thr Ile Ile Ile Gly His Ser Ser Gly Ala Ile Ala
65                  70                  75                  80 gcc atg agg tat gca gag aca cat cag gta tac gct ctc gta ttg gtg       288
Ala Met Arg Tyr Ala Glu Thr His Gln Val Tyr Ala Leu Val Leu Val
                85                  90                  95 tct gca tac aca tca gac ttg gga gat gaa aat gag cgt gca agt ggg       336
Ser Ala Tyr Thr Ser Asp Leu Gly Asp Glu Asn Glu Arg Ala Ser Gly
            100                 105                 110 tac ttc agc cgc ccc tgg cag tgg gag aag atc aag gcc aac tgc cct       384
Tyr Phe Ser Arg Pro Trp Gln Trp Glu Lys Ile Lys Ala Asn Cys Pro
        115                 120                 125 cac att ata cag ttt ggc tct act gat gac ccc ttc ctt ccc tgg aag       432
His Ile Ile Gln Phe Gly Ser Thr Asp Asp Pro Phe Leu Pro Trp Lys
    130                 135                 140 gaa caa caa gaa gtg gca gat agc tgg acg cca aat tgt aca aat tca       480
Glu Gln Gln Glu Val Ala Asp Ser Trp Thr Pro Asn Cys Thr Asn Ser
145                 150                 155                 160 ctg acc gtg gtc act ttc aga aca cag agt tcc atg aac tga               522
Leu Thr Val Val Thr Phe Arg Thr Gln Ser Ser Met Asn
                165                 170
```

```
<210> SEQ ID NO 10
<211> LENGTH: 173
<212> TYPE: PRT
<213> ORGANISM: Mus musculus

<400> SEQUENCE: 10
```

```
Met Ala Ser Pro Asn Lys Ala Val Ile Val Pro Gly Asn Gly Gly Gly
1               5                   10                  15
```

-continued

```
Asp Val Ala Thr His Gly Trp Tyr Gly Trp Val Lys Lys Gly Leu Glu
             20                  25                  30

Gln Ile Pro Gly Phe Gln Cys Leu Ala Lys Asn Met Pro Asp Pro Ile
         35                  40                  45

Thr Ala Arg Glu Ser Ile Trp Leu Pro Phe Met Glu Thr Glu Leu His
     50                  55                  60

Cys Asp Glu Lys Thr Ile Ile Gly His Ser Ser Gly Ala Ile Ala
 65                  70                  75                  80

Ala Met Arg Tyr Ala Glu Thr His Gln Val Tyr Ala Leu Val Leu Val
                 85                  90                  95

Ser Ala Tyr Thr Ser Asp Leu Gly Asp Glu Asn Glu Arg Ala Ser Gly
            100                 105                 110

Tyr Phe Ser Arg Pro Trp Gln Trp Glu Lys Ile Lys Ala Asn Cys Pro
        115                 120                 125

His Ile Ile Gln Phe Gly Ser Thr Asp Pro Phe Leu Pro Trp Lys
    130                 135                 140

Glu Gln Gln Glu Val Ala Asp Ser Trp Thr Pro Asn Cys Thr Asn Ser
145                 150                 155                 160

Leu Thr Val Val Thr Phe Arg Thr Gln Ser Ser Met Asn
                165                 170
```

```
<210> SEQ ID NO 11
<211> LENGTH: 714
<212> TYPE: DNA
<213> ORGANISM: Mus musculus

<400> SEQUENCE: 11
cagagccctg aaaggttgtt gcatgagccc gtgaaagtgg agtttcagtg gtagtggata      60
gcataggaca ctggagacac agttcatgtc cagcattcat ggagtgggag cagagagttc     120
cctgaagctc actggctagt attcttgcta aaccaatgag ctccaaattc acagatcttg     180
tcgcaaaacc caaatgtaat gtggaaatga aggaaaagaa acacccaac actgactgaa      240 tatggtgaca ctcccttta atgccagcac tcaggagaca aaaagcaggc agatcttttg      300
tgagttctag gccagtctgg tttacataga cagctccagg ccagtaaggg gctacgtaat     360
gaaactgtct taaacaaatt aaggaacgtt catttgaaaa aaaataaacc ttccttaaag     420
aagtattggt acaactaata aaaagataac acattatgag cacgctgttg ccagcacata     480
agggatgtgg agtatgagaa cgctggaaaa ggggtaaatc aaagataatt aatatttgat     540
ggtaattcac aggtttgagt ttagctgcct gtgctttagc cagaaaatgc gtaggcctgc     600
aggtatccaa gaactacaat tcccagaagt ccgcagtgca ggctctgggc cggatgtagt     660
cttggtctga gagctgctgg tccaagctgg gcaaggtctc ccacgtctac attc          714

<210> SEQ ID NO 12
<211> LENGTH: 30
<212> TYPE: DNA
<213> ORGANISM: Artificial Sequence
<220> FEATURE:
<223> OTHER INFORMATION: Antisense

<400> SEQUENCE: 12
aatcactgcc ttggtagggg acaccattaa                                       30

<210> SEQ ID NO 13
<211> LENGTH: 33
<212> TYPE: DNA
```

```
<213> ORGANISM: Artificial Sequence
<220> FEATURE:
<223> OTHER INFORMATION: Antisense

<400> SEQUENCE: 13
tcagttcatg gaactctgtg ttctgaaagt gac                                 33

<210> SEQ ID NO 14
<211> LENGTH: 15
<212> TYPE: DNA
<213> ORGANISM: Artificial Sequence
<220> FEATURE:
<223> OTHER INFORMATION: Primer

<400> SEQUENCE: 14
atggtctctc ctagc                                                     15

<210> SEQ ID NO 15
<211> LENGTH: 13
<212> TYPE: DNA
<213> ORGANISM: Artificial Sequence
<220> FEATURE:
<223> OTHER INFORMATION: Primer

<400> SEQUENCE: 15
gagttccatg aac                                                       13
```